(12) United States Patent
Krog et al.

(10) Patent No.: US 8,652,785 B2
(45) Date of Patent: Feb. 18, 2014

(54) METHOD OF SCREENING A MODULATOR OF ENDOTHELIAL NO SYNTHASE COMPRISING THE USE OF HEME BINDING PROTEIN 1

(75) Inventors: Alexandra Krog, Bodenheim Nackenheim (DE); Jochen Kruip, Erzhausen (DE); Paulus Wohlfart, Bensheim (DE); Johann Gassenhuber, Wiesbaden (DE); Kathrin Heermeier, Hochheim (DE); Hartmut Strobel, Liederbach (DE); Natalie Karst, Paris (FR); Alexandra Ferrier, Paris (FR); Christian Viskov, Ris Orangis (FR)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 13/131,914

(22) PCT Filed: Nov. 27, 2009

(86) PCT No.: PCT/EP2009/065989
§ 371 (c)(1),
(2), (4) Date: Aug. 23, 2011

(87) PCT Pub. No.: WO2010/063652
PCT Pub. Date: Jun. 10, 2010

(65) Prior Publication Data
US 2011/0306553 A1  Dec. 15, 2011

(30) Foreign Application Priority Data
Dec. 4, 2008  (EP) .................................... 08291148

(51) Int. Cl.
*C12Q 1/68*  (2006.01)

(52) U.S. Cl.
USPC .......................................................... 435/6.13

(58) Field of Classification Search
None
See application file for complete search history.

(56) References Cited

U.S. PATENT DOCUMENTS

| 6,794,158 B2 * | 9/2004 | Ingraham et al. | 435/18 |
| 2002/0048581 A1 | 4/2002 | King | |
| 2006/0078559 A1 * | 4/2006 | Migeotte et al. | 424/143.1 |
| 2011/0306553 A1 * | 12/2011 | Krog et al. | 514/16.4 |

FOREIGN PATENT DOCUMENTS

| EP | 1 607 745 A2 | 12/2005 |
| WO | WO 98/15830 | 4/1998 |
| WO | WO 03/040120 A1 | 5/2003 |
| WO | WO 2004/041170 A2 | 5/2004 |
| WO | WO 2009/044143 A2 | 4/2009 |

OTHER PUBLICATIONS

Schafer et al, 2004. The European Journal of Heart Failure. 6: 151-159.*
ECL Plus instructions, Amersham, 2002, no author listed, 28 pages.*
Wells (1990) Biochemistry 29(37): 8509-8517.*
Ngo et al (1994) "The Protein Folding Problem and Tertiary Structure Prediction, Chapter 14: Computational Complexity Protein Structure Prediction, and the Levinthal Paradox" pp. 433-440 and 492-495 only.*
Bork (2000) Genome Research 10:398.*
Skolnick et al (2000) Trends in Biotech. 18(1): 34.*
Doerks et al (1998) Trends in Genetics 14(6): 248.*
Brenner (1999) Trends in Genetics 15(4): 132.*
Schafer et al, 2004. European Journal of Heart Failure. 6: 151-159.*
International Search Report for WO2010/063652 dated Jun. 10, 2010.
Forstermann et al., Endothelial Nitric Oxide Synthase in Vascular Disease From Marvel to Menace, Circulation, 2006, pp. 1708-1714, vol. 113.
Searles, C., Transcritional and posttranscriptional regulation of endothelial nitric oxide synthase expression, Am. J. Physiol. Cell Physiol. May 31, 2005. pp. C803-C816, vol. 291.
Thrower et al., A Quantitave Solid-Phase Binding Assay for Tubulin, Methods in Cell Biology, 1993. pp. 129-145, vol. 37.
Ullman et al., Luminescent oxygen channeling immunoassay: Measurement of particle binding kinetics by chemiluminescence, PNAS, vol. 91, Jun. 1994, pp. 5426-5430.

* cited by examiner

*Primary Examiner* — Zachary Howard
(74) *Attorney, Agent, or Firm* — Lathrop & Gage LLP; James H. Velema, Esq.

(57) ABSTRACT

The present invention relates to a method of screening for a modulator of endothelial NO synthase (eNOS) expression, a method of diagnosing a cardiovascular disease in a subject, the use of HEBP-1 for the identification of a medicament for preventing and/or treating a disease involving eNOS dysfunction, particularly a cardiovascular disease, the use of HEBP-1 for the detection of a component of eNOS signal transduction, and the use of HEBP1 for the regulation of eNOS promoter activity.

10 Claims, 3 Drawing Sheets

Figure 1:
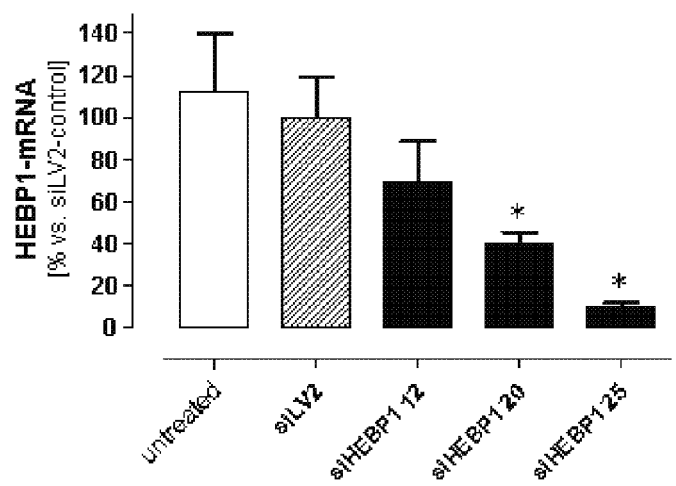

SEQUENCE LISTING

```
<160> NUMBER OF SEQ ID NOS: 25

<210> SEQ ID NO 1
<211> LENGTH: 25
<212> TYPE: DNA
<213> ORGANISM: Artificial Sequence
<220> FEATURE:
<223> OTHER INFORMATION: TaqMan probe

<400> SEQUENCE: 1
ggtgacaaca ggtccctcat agcta                                            25

<210> SEQ ID NO 2
<211> LENGTH: 25
<212> TYPE: DNA
<213> ORGANISM: Artificial Sequence
<220> FEATURE:
<223> OTHER INFORMATION: TaqMan probe

<400> SEQUENCE: 2
```

-continued tcagaaagga gttcgtgaag tgacc                                              25

<210> SEQ ID NO 3
<211> LENGTH: 25
<212> TYPE: DNA
<213> ORGANISM: Artificial Sequence
<220> FEATURE:
<223> OTHER INFORMATION: TaqMan probe

<400> SEQUENCE: 3
ggcgcctggt caccagggct gcttt                                              25

<210> SEQ ID NO 4
<211> LENGTH: 25
<212> TYPE: DNA
<213> ORGANISM: Artificial Sequence
<220> FEATURE:
<223> OTHER INFORMATION: TaqMan probe

<400> SEQUENCE: 4
ctcgttcctg ttcagaaggc cggga                                              25

<210> SEQ ID NO 5
<211> LENGTH: 25
<212> TYPE: DNA
<213> ORGANISM: Artificial Sequence
<220> FEATURE:
<223> OTHER INFORMATION: TaqMan probe

<400> SEQUENCE: 5
cacttgagct gacacacaat tgggg                                              25

<210> SEQ ID NO 6
<211> LENGTH: 25
<212> TYPE: DNA
<213> ORGANISM: Artificial Sequence
<220> FEATURE:
<223> OTHER INFORMATION: TaqMan probe

<400> SEQUENCE: 6
tgtctattcc atgcagtttg gtggt                                              25

<210> SEQ ID NO 7
<211> LENGTH: 25
<212> TYPE: DNA
<213> ORGANISM: Artificial Sequence
<220> FEATURE:
<223> OTHER INFORMATION: TaqMan probe

<400> SEQUENCE: 7
ggaaagctgg ggcggaggga tttgt                                              25

<210> SEQ ID NO 8
<211> LENGTH: 25
<212> TYPE: DNA
<213> ORGANISM: Artificial Sequence
<220> FEATURE:
<223> OTHER INFORMATION: TaqMan probe

<400> SEQUENCE: 8
taaggacgga aagagcttga caaaa                                              25

<210> SEQ ID NO 9
<211> LENGTH: 25
<212> TYPE: DNA
<213> ORGANISM: Artificial Sequence

```
<220> FEATURE:
<223> OTHER INFORMATION: TaqMan probe

<400> SEQUENCE: 9
cccctgctgg gccactgatt gtgcc                                        25

<210> SEQ ID NO 10
<211> LENGTH: 25
<212> TYPE: DNA
<213> ORGANISM: Artificial Sequence
<220> FEATURE:
<223> OTHER INFORMATION: TaqMan probe

<400> SEQUENCE: 10
gcatggtgtg ctctgcttat gataa                                        25

<210> SEQ ID NO 11
<211> LENGTH: 25
<212> TYPE: DNA
<213> ORGANISM: Artificial Sequence
<220> FEATURE:
<223> OTHER INFORMATION: TaqMan probe

<400> SEQUENCE: 11
atgagagatg tctacattgt gcagg                                        25

<210> SEQ ID NO 12
<211> LENGTH: 25
<212> TYPE: DNA
<213> ORGANISM: Artificial Sequence
<220> FEATURE:
<223> OTHER INFORMATION: TaqMan probe

<400> SEQUENCE: 12
tcaaatctgt ctacgtggtc ctgga                                        25

<210> SEQ ID NO 13
<211> LENGTH: 25
<212> TYPE: DNA
<213> ORGANISM: Artificial Sequence
<220> FEATURE:
<223> OTHER INFORMATION: TaqMan probe

<400> SEQUENCE: 13
gaatggagag agctttgcag ctgcc                                        25

<210> SEQ ID NO 14
<211> LENGTH: 25
<212> TYPE: DNA
<213> ORGANISM: Artificial Sequence
<220> FEATURE:
<223> OTHER INFORMATION: TaqMan probe

<400> SEQUENCE: 14
gtatctcatc aacgccaggc tgacg                                        25

<210> SEQ ID NO 15
<211> LENGTH: 25
<212> TYPE: DNA
<213> ORGANISM: Artificial Sequence
<220> FEATURE:
<223> OTHER INFORMATION: TaqMan probe

<400> SEQUENCE: 15
aacctcaagg tggcctgtga gaaga                                        25
```

-continued

```
<210> SEQ ID NO 16
<211> LENGTH: 25
<212> TYPE: DNA
<213> ORGANISM: Artificial Sequence
<220> FEATURE:
<223> OTHER INFORMATION: TaqMan probe

<400> SEQUENCE: 16
cccaggagat tgcagtgga tgact                                                25

<210> SEQ ID NO 17
<211> LENGTH: 25
<212> TYPE: DNA
<213> ORGANISM: Artificial Sequence
<220> FEATURE:
<223> OTHER INFORMATION: TaqMan probe

<400> SEQUENCE: 17
gaagttcccc atgagggtcc aatgt                                               25

<210> SEQ ID NO 18
<211> LENGTH: 25
<212> TYPE: DNA
<213> ORGANISM: Artificial Sequence
<220> FEATURE:
<223> OTHER INFORMATION: TaqMan probe

<400> SEQUENCE: 18
atggaaggct ggatgaaaaa gaaag                                               25

<210> SEQ ID NO 19
<211> LENGTH: 25
<212> TYPE: DNA
<213> ORGANISM: Artificial Sequence
<220> FEATURE:
<223> OTHER INFORMATION: TaqMan probe

<400> SEQUENCE: 19
gtgcgggaat tgctagctgt tccag                                               25

<210> SEQ ID NO 20
<211> LENGTH: 25
<212> TYPE: DNA
<213> ORGANISM: Artificial Sequence
<220> FEATURE:
<223> OTHER INFORMATION: TaqMan probe

<400> SEQUENCE: 20
cggtacgccc tccaggtgtg gcggc                                               25

<210> SEQ ID NO 21
<211> LENGTH: 25
<212> TYPE: DNA
<213> ORGANISM: Artificial Sequence
<220> FEATURE:
<223> OTHER INFORMATION: TaqMan probe

<400> SEQUENCE: 21
gcaaatgccc caggtgatca tggag                                               25

<210> SEQ ID NO 22
<211> LENGTH: 25
<212> TYPE: DNA
<213> ORGANISM: Artificial Sequence
<220> FEATURE:
<223> OTHER INFORMATION: TaqMan probe

<400> SEQUENCE: 22
```

```
ttataaacgt gatgttggaa aagta                                      25

<210> SEQ ID NO 23
<211> LENGTH: 25
<212> TYPE: DNA
<213> ORGANISM: Artificial Sequence
<220> FEATURE:
<223> OTHER INFORMATION: TaqMan probe

<400> SEQUENCE: 23
tgcccaacac gctaccctg tccag                                       25

<210> SEQ ID NO 24
<211> LENGTH: 29
<212> TYPE: DNA
<213> ORGANISM: Artificial Sequence
<220> FEATURE:
<223> OTHER INFORMATION: Primer

<400> SEQUENCE: 24
cgtgaattcg atcaagaact cgctgttcg                                  29

<210> SEQ ID NO 25
<211> LENGTH: 20
<212> TYPE: DNA
<213> ORGANISM: Artificial Sequence
<220> FEATURE:
<223> OTHER INFORMATION: Primer

<400> SEQUENCE: 25
taaacgggcc ctctagactc                                            20
```

METHOD OF SCREENING A MODULATOR OF ENDOTHELIAL NO SYNTHASE COMPRISING THE USE OF HEME BINDING PROTEIN 1

The present invention relates to a method of screening for a modulator of endothelial NO synthase (eNOS) expression, a method of diagnosing a cardiovascular disease in a subject, the use of HEBP-1 for the identification of a medicament for preventing and/or treating a disease involving eNOS dysfunction, particularly a cardiovascular disease, the use of HEBP-1 for the detection of a component of eNOS signal transduction, and the use of HEBP1 for the regulation of eNOS promoter activity.

Nitric oxide synthases (EC 1.14.13.39; NOSs) were discovered in 1998 and at that date the physiological importance of their product, nitric oxide (NO), which is the smallest bioactive molecule in mammals, was not known. In the meantime, it was found that NO is an important messenger at the regulation of vascular tone in the cardiovascular system, as second messenger in the central nervous system and as defense mechanism against bacterial and tumor cells. In 1989, the Nobel Price for medicine was awarded to Robert Furchgott, Ferid Murad and Luis J. Ignaro who identified NO as messengers of mammalian cells.

NOSs are members of a family of related enzymes encoded by separate genes. NOS is one of the most regulated enzymes in biology. There are three known isoforms, two are constitutive (cNOS) and the third is inducible (iNOS). Cloning of NOS enzymes indicates that cNOS includes both brain constitutive (NOS1, nNOS or neuronal NOS) and endothelial constitutive (NOS3, eNOS, cNOS or endothelial NOS) genes, the third is the inducible (NOS2, iNOS or inducible NOS) gene.

In the brain, nNOS is a soluble enzyme having a molecular weight of 161 kDa and represents the largest NOS isoform. This isoform is constitutively expressed mainly in neuronal cells and in the brain and produces only low amounts of NO. The regulation of enzymatic activity is mediated by $Ca^{2+}$ via calmodulin. However, its enzymatic activity is also influenced by phosphorylation via $Ca^{2+}$ calmodulin-dependent protein kinase 2 as well as protein kinase A, C and G. In the brain, NO is important for the regulation of signal transaction at synapsis. Peripheral blood vessels and smooth muscle cells are often innervated by nerves which release NO and act antagonistic to the sympathicus. Additionally, large amounts of nNOSs were detected in skeletal muscle, in which NO controls muscle contractility and local blood flow. Inducible NOS is expressed in macrophages, but also in other cells after induction by bacterial LPS or cytokines As nNOS, iNOS is a mostly soluble protein having a molecular weight of 131 kDa, which releases huge amounts of NO. iNOS is regulated transcriptionally by various stimuli. After induction of its expression, the NO release serves as cytotoxic principle of macrophages by damaging microorganisms and parasites as well as tumor cells. However, NO might also attack healthy body cells and induce damages of the surrounding tissue. Most of the inflammatory and autoimmune diseases are characterized by the presence of huge amounts of activated macrophages and neutrophil granulocytes. Furthermore, iNOS is also important in the pathology of septic shock, which is characterized by massive arterial vasodilataion, hypotony and microvascular damages.

Finally, endothelial NOS is responsible for the major part of vascularly produced NO, which protects against arteriosclerosis and thrombosis. Intact eNOS constitutes a central key in the physiological maintenance of the vascular homeostasis and plays a key role in the pathophysiology of the cardiovascular system. Release of NO by eNOS in vascular endothelium is mediated at basal conditions by stimulation of a series of receptor agonists such as bradykinine, acetylcholine and histamine as well as sheer stress of flowing blood. NO leads to dilatation of all types of blood vessels by stimulation of soluble guanylyl cyclase and increase of concentration of cGMP in smooth muscle cells. Accordingly, NO from endothelial cells is an important endogeneous vasodilative counterpart of vasoconstriction by the sympathicus or the renine angiotensine system.

In addition to its vasodilative properties, endothelial NO has a series of vasoprotective and antisclerotic properties. The NO released to vascular lumen is a potent inhibitor of platelet aggregation and adhesion at the vessel wall. Apart from the protection against thrombosis, release of growth factors from platelets is inhibited, which could stimulate a proliferation of smooth muscle cells. In rabbits and mice it was shown that the genetic or pharmacological inhibition of eNOS leads to progressive arteriosclerosis. Furthermore, the expression of genes involved in the arteriogenesis may be modulated by endothelial NO. This holds particularly true for chemotactic protein from monocytes (MCP1), surface molecules such as CD11/CD18, P-selectine, the vascular cell adhesion molecule 1 VCAM-1 and the intracellular adhesion molecule ICAM 1. Accordingly, adhesion and infiltration of lipocytes in the vessel wall are prevented, thereby protecting against the early phase of arteriogenesis. Furthermore, NO inhibits DNA synthesis, mitogenesis and proliferation of vascular smooth muscle cells. It is assumed that antiproliferated effects are mediated by cGMP. Moreover, NO may have direct effects by S-nitrosylation of proteins such as an anti-apoptotic effect in endothelial cells by nitrosylation of caspase 3.

A series of cardiovascular diseases has been associated with a lack of bio-available NO due to reduced synthesis and/or increased degradation of NO. Other classical symptoms and diseases include hypocholesterolemia, diabetes mellitus, hypertony and adverse effects mediated by smoking. As detailed above, the pathology of different cardiovascular diseases is usually based on a lack of NO as result of endothelial dysfunction. The NO bioactivity may be due to reduced expression and/or activity of eNOS, eNOS decoupling, increased degradation of NO or reduced responsiveness of the NO effector systems.

Conservative therapy with organic nitrates is associated with multiple disadvantages due to the release of huge amounts of NO. Particularly at permanent medication, a significant reduction of the effect of nitrate is observed, which is referred to as "nitrate tolerance". A nitrate-free period of from 6-8 hours is necessary in order to obtain the full effect of the nitrate. Additionally, typical adverse effects are nitrate headache, reddened skin ("flash") and the risk of strong decrease in blood pressure with reflectory tachycardia. Accordingly, the identification of new drugs for a permanent therapy, which may induce expression of functional eNOS and which could permanently increase the amount of bio-available NO in contrast to nitrate, is an interesting and valuable target of research. Due to its important physiological and pathophysiological function in the animal (including human) body, it is important to detect new ways of modulate eNOS activity.

Accordingly, it was an object of the present invention to detect alternative mechanisms of modulating eNOS activity.

Surprisingly, it was found that Heme binding protein 1 (HEBP1) is involved in the activation of eNOS expression. Particularly, it was found that the activity of eNOS promoter was significantly reduced when HEBP1 was switched off by RNA technology.

Accordingly, means and methods of interacting with HEBP1 may be used in order to regulate or change eNOS promoter activity and/or eNOS expression.

Therefore, in a first aspect, the present invention relates to a method of screening for a modulator of endothelial NO synthase (eNOS) expression, the method comprising
providing a test system comprising heme binding protein 1 (HEBP1) or a functionally active variant thereof,
contacting the test system with an agent, and
detecting an effect of the agent on the test system, thereby identifying the agent as a modulator of eNOS expression.

As detailed above, eNOS, also known as nitric oxide synthase 3 (NOS3), generates NO in blood vessels and is involved with regulating vascular function. It is specifically expressed in different arterial and venous endothelial cell types. However, it could also be shown that eNOS is expressed in human placenta, tubular kidney epithelial cells and colon cells of rabbit and eNOS immunoreaction was also detected in neurons of rat hippocampus and other brain regions. eNOS is constitutively expressed and releases low amounts of NO in comparison to iNOS.

The enzyme eNOS is present as homodimer, wherein each monomer is composed of the several subunits (A schematic illustration of iNOS is shown in Forstermann and Monzen, 2006, Circulation 113:1708-1714). The C-terminal reductase domain binds nicotine amide adenine dinucleotide phosphate (NADPH), flavin mononucleotide (FMN) and flavin adenine dinucleotide (FAD) and is linked to a calmodulin binding domain with oxygenase domain. The oxygenase domain has a prostatic Heme group and binds 6(R)-5,6,7,8-tetrahydrobiopterin ($BH_4$), molecular oxygen and L-arginine The reductase domain of the monomer is linked to the N-terminal oxygenase domain of the second monomer. All NOS isoenzymes catalyze flavin-mediated electron transfer from C-terminal-bound NADPH to the heme at the N-terminal domain. Electron transfer in the reductase domain from NADPH to flavin as well as from the reductase domain to the heme of the oxygenase domain is increased by calcium-induced binding from calmodulin to NOS. At the heme group, the electrons are used for the reduction and activation of molecular oxygen. The oxidation of L-agenine to L-citroline occurs via two successive monooxygenation reactions producing $N^{\omega}$-hydroxy-L-agenine (NOHLA) as an intermediate, thereby producing NO.

As detailed above, endothelial NO synthase (eNOS) dysfunction is involved in a series of diseases. It could be proven that eNOS expression is reduced in various diseases, including cardiovascular diseases such as heart failure and myocardial infarction. Surprisingly, it has been found that heme binding protein 1 (HEBP1) is a factor modulation eNOS expression, particularly by interacting with the eNOS promoter. This fact can be used in order to detect modulators of eNOS expression, which forms a potential therapeutic for the treatments of diseases characterized by altered eNOS expression.

The claimed method of screening for a modulator includes providing a test system comprising HEBP1. As shown in the context of the present invention, HEBP1 is a protein interacting with eNOS promoter and thereby altering eNOS expression. HEBP1 is also referred to heme binding protein 1, HBP, HEBP or p22HBP. It is assumed that HEBP1 may act in the binding of free porphyrinogens that may be present in the cell and thus facilitate removal of these potentially toxic compounds. It binds with a high affinity to one molecule of heme or porphyrins, wherein it has similar affinities to metalloporphyrins, free porphyrins and N-methylprotoporphyrin.

The amino acid sequence of the human protein consists of 189 amino acids and is available at PubMed under the accession no. NP_057071. However, the HEBP1 protein may be also derived form any other species and the sequence of HEBP1 proteins of other species has already been published. Examples include musculus (accession no. NP_038574, referred to as HEBP1), pan troglodytes (accession no. XP_528742, referred to as LOC473371), *Gallus gallus* (accession no. NP_001025925, referred to as RCJMB04_2k3), *Canis familiaris* (accession no. XP_534884, referred to as NOC477690) and *Rattus norwegicus* (accession no. XP_342776, referred to as HEBP1_predicted).

In addition to any natural occurring HEBP1 variant, such as a species variant or splice variant, modified HEBP1 proteins may be also used. It should be noted that the modified HEBP1 protein or HEBP1 variant is a functionally active variant, in that the variant maintains its biological function to interact with eNOS promoter and modulate eNOS expression. Preferably, maintenance of biological function, e.g. regulation of eNOS expression, is defined as having at least 50%, preferably at least 60%, more preferably at least 70%, 80% or 90%, still more preferably 95% of the modulator activity of the natural occurring HEBP1. The biological activity may be determined as described in the examples, particularly in examples 1, 2, 3 or 4 (e.g. by using a eNOS promoter reporter cell line such as EA.crs03 or biotin-labeled transcription enhancers such as A012 or A013 or RT-PCR for the determination of mRNA levels such as eNOS mRNA or quenching of tryptophan fluorescence or fluorescence polarization or animal models).

The variant may be a molecule having a domain composed of a naturally occurring HEBP1 protein and at least one further component. For example, the protein may be coupled to a marker, such as a tag used for purification purposes (e.g. 6 His (or HexaHis) tag, Strep tag, HA tag, c-myc tag or glutathione S-transferase (GST) tag). If a e.g. highly purified HEBP1 protein or variant should be required, double or multiple markers (e.g. combinations of the above markers or tags) may be used. In this case the proteins are purified in two or more separate chromatography steps, in each case utilizing the affinity of a first and then of a second tag. Examples of such double or tandem tags are the GST-His-tag (glutathione-S-transferase fused to a polyhistidine-tag), the 6×His-Strep-tag (6 histidine residues fused to a Strep-tag), the 6×His-tag100-tag (6 histidine residues fused to a 12-amino-acid protein of mammalian MAP-kinase 2), 8×His-HA-tag (8 histidine residues fused to a haemagglutinin-epitope-tag), His-MBP (His-tag fused to a maltose-binding protein, FLAG-HA-tag (FLAG-tag fused to a hemagglutinin-epitope-tag), and the FLAG-Strep-tag. The marker could be used in order to detect the tagged protein, wherein specific antibodies could be used. Suitable antibodies include anti-HA (such as 12CA5 or 3F10), anti-6 His, anti-c-myc and anti-GST. Furthermore, the HEBP1 protein could be linked to a marker of a different category, such as a fluorescence marker or a radioactive marker, which allows for the detection of HEBP1. In a further embodiment, HEBP1 could be part of a fusion protein, wherein the second part could be used for detection, such as a protein component having enzymatic activity.

In another embodiment of the present invention, the HEBP1 variant could be a HEBP fragment, wherein the fragment is still capable of interacting with the eNOS promoter and regulating eNOS expression. This may include HEBP1 proteins with short C- and/or N-terminal deletions (e.g. deletions of at most 20, 19, 18, 17, 16, 15, 14, 13, 12, 11, 10, 9, 8, 7, 6 5, 4, 3, 2, or 1 amino acid). Additionally, the HEBP1 fragment may be further modified as detailed above for the HEBP1 protein.

Alternatively or additionally, the HEBP1 protein or variant thereof as described above may comprise one or more amino acid substitution(s), particularly in regions not involved in the interactions with the eNOS promoter and regulation of eNOS expression. However, conservative amino acid substitutions, wherein an amino acid is substituted with a chemically related amino acid are preferred. Typical conservative substitutions are among the aliphatic amino acids, are among the amino acids having aliphatic hydroxyl side chains, are among the amino acids having acidic residues, among the amid derivates, among the amino acids with basic residues, or the amino acids having aromatic residues. The HEBP1 protein or fragment or variant with substitution may be modified as detailed above for the HEBP1 protein or fragment or variant. In the following description of the invention all details given with respect to HEBP1 protein also relate to functionally active variants thereof, unless stated otherwise.

However, most preferably, the HEBP1 protein is a naturally occurring HEBP1 protein, still more preferably, a naturally occurring human HEBP1 protein.

As detailed above, the test system comprises the HEBP1 protein or functionally active variants thereof. The test system may also comprise further elements such as means for detecting the effect of a modulator on the test system in order to identify an agent as a modulator of the eNOS expression. Suitable means for detection of the effect of a modulator are detailed throughout the present description. The test system may be in a cellular system or a cell-free system, as appropriate under the prevailing conditions.

For the method of the present invention, the test system comprising HEBP1 or a functionally active variant thereof is contacted with an agent. The agent tested with the method of the present invention may be any test substance or test compound of any chemical nature. It may already be known as a drug or medicament for a disease. Alternatively, it may be a known chemical compound not yet known to have a therapeutic effect in another embodiment and the compound may be a novel or so far unknown chemical compound. The agent may be also a mixture of test substances or test compounds.

In one embodiment of the screening method of the present invention, the test substance is provided in form of a chemical compound library. Chemical compound libraries include a plurality of chemical compounds and have been assembled from any of multiple sources, including chemical synthesized molecules or natural products, or have been generated by combinatorial chemistry techniques. They are especially suitable for high-throughput screening and may be comprised of chemical compounds of a particular structure or compounds of a particular organism such as a plant. In the context of the present invention, the chemical compound library is preferably a library comprising proteins and polypeptides or small organic molecules. Preferably a small organic molecule is less than 500 daltons in size, particularly a soluble, non-oligomeric, organic compound.

In the context of the present invention, the test system is contacted with the agent for a time and under conditions suitable for modulating eNOS expression and detecting the same. Suitable conditions include appropriate temperature and solution to avoid e.g. denaturation of proteins involved or to maintain viable cells, if present. Suitable conditions will depend from the particular test system chosen and the skilled person will be able to select the same based on his general knowledge.

After the contacting of the test system with the agent, the effect of the agent on the test system is detected. In the following, a series of different detection systems will be described in more detail. However, it should be understood that these are exemplary and other test systems may be also appropriate.

If the agent has a specific and significant effect on the test system, the agent is identified as modulator of eNOS expression. A modulator of eNOS expression in the context of the present invention means an agent changing, either increasing or decreasing, eNOS expression. Preferably, eNOS expression is increased. In the context of the present invention, eNOS expression is modified, i.e. decreased or preferably increased, in comparison to a control, if the eNOS expression in suitable cell contacted with the modulator is significant lower or higher, respectively, than that of a control (i.e. the same cell not contacted with the modulator). The person skilled in the art knows statistical procedures to assess whether two values are significantly different from each other such as Student's t-test or chi-square tests.

In a preferred embodiment, the eNOS expression amounts to at least 110%, preferably at least 125%, more preferably at least 150%, 160%, 170%, 180% or 190%, still more preferably at least 200% and most preferably at least 300% of the control.

However, the method of the invention does not require that the effect of the modulator on the eNOS expression is determined within that method. It is noted that the screening method may or may not encompass a step, wherein eNOS expression is measured. Alternatively to measuring the eNOS expression, detection methods indicative of the modulation of eNOS expression may be used. Especially for high-throughput screening, it might be preferable to use a very easy and robust detection system, which comprises as few components as possible. In one embodiment of the present invention, the test system may only comprise the HEBP1 protein (or functional active variant thereof) and means for detecting the binding of the agent/modulator to the protein in the absence of further components of the signal transduction involving HEBP1 and eNOS. Such a system may be, for example, a system wherein either the agent to be tested or the HEBP1 protein or functionally active variant thereof is immobilized on a carrier. Binding of the agent to the HEBP1 protein or functionally active variant may be detected whereby the non-immobilized binding partner is labeled with a detectable marker. The immobilized component may be immobilized on a single material or on a plurality of different materials that are capable of binding a biomolecule or a variety of biomolecules based on their physical characteristics. Such materials include, but are not limited to, anion exchange materials, cation exchange materials, metal chelators, peptides, antibodies, polymers (synthetic or natural), paper etc.

The immobilized component may be contacted with a mobile (i.e. not immobilized) potential binding partner, wherein the unbound mobile binding partner is removed after a time sufficient to allow for binding. Binding of mobile and immobilized components may be detected due to the presence of the marker of the mobile binding partner at the location of immobilization of the immobilized partner. For example, a series of different agents, such as proteins, could be immobilized in a multi-well plate and could be incubated with labeled HEBP1 protein. In those wells where the marker is detected, binding between the agent and the HEBP1 protein occurred. The respective agent may be identified as a potential modulator of eNOS expression.

The component, particularly the protein, may be labeled in a variety of ways to allow sufficient detection or purification.

Common labeling methods may be used for labeling of one or more functional groups on the surface of the component. For protein, these could be for example the primary amino groups, present at the N-terminal of each polypeptide chain and the side chain of lysine residues; sulphhydryl groups, present on cysteine residues made available by treating disulphide bonds with reducing agent or by modifying lysine residues with a reagent such as SATA; or carbohydrate groups, usually present in the Fc region of antibodies, which may be oxidated to create active aldehydes for coupling. The component or protein may be labeled with a series of different agents, such as biotin (for avidine-biotin chemistry), enzymes, activated fluorescent dyes for labeling amines, sulphhydryls or other functional groups with e.g. FITC, fluorescein, rhodamine, Cy dyes or Alexa fluos. Radioactive label such as $^3$H, $^{32}$P, $^{35}$S, $^{125}$I or $^{14}$C as well as common enzyme labels including penicillinase, horseradish peroxidase and alkaline phosphatase may be used as well.

For the method of the invention any suitable detection may be used. Suitable methods may be chosen depending from the characteristics of the test system and agents to be tested. As detailed above, HEBP1 is involved in the signal transduction of eNOS expression. Accordingly, the interaction of the agents with the HEBP1 (or variant thereof) or a component upstream in the signal transduction of HEBP1 may be determined. Interaction may be determined directly or indirectly. "Directly" means that the binding of the agent to HEBP1 is determined (e.g. using a labeled marker in order to detect HEBP1/agent complexes). "Indirectly" means that an effect of HEBP1 downstream in the signal transduction is determined (e.g. activity of eNOS promoter, level of eNOS mRNA or amount of eNOS protein). Suitable methods are detailed e.g. in the examples.

In the first case agent protein interactions are measured. A series of tests are known in the art in which the test system may be used and to which the test system may be adapted. This may be a heterogeneous or homogeneous assay. As used herein, a heterogeneous assay is an assay which includes one or more washing steps, whereas in a homogeneous assay such washing steps are not necessary. The reagents and compounds are only mixed and measured.

In an embodiment the assay is an ELISA (enzyme linked immuno sorbent assay), a DELFIA (dissociation enhanced lanthanide fluoro immuno assay), an SPA (scintillation proximity assay) a flashplate assay, a FRET (fluorescence resonance energy transfer) assay, TR-FRET (time-resolved fluorescence resonance energy transfer) assay, a FP (fluorescence polarisation) assay, an ALPHA (amplified luminescent proximity homogenous assay), an EFC (enzyme fragment complementation) assay, a two hybrid assay or a coimmunoprecipitation assay.

ELISA (enzyme linked immuno sorbent assay)-based assays are offered by various companies. It is a biochemical technique used to detect the presence of an antibody or an antigen in a sample. Performing an ELISA involves at least one antibody with specificity for a particular antigen (e.g a segment of the first or second protein). In general, an unknown amount of antigen in a sample is immobilized on a surface. One then washes a particular antibody over the surface. This antibody is linked to an enzyme that produces a detecable signal such as a change in colour or fluorescene. For example, the sample with an unknown amount of antigen is immobilized on a solid support (usually a microtiter plate) either non-specifically (via adsorption to the surface) or specifically (via capture by another antibody specific to the same antigen, in a "sandwich" ELISA). After the antigen is immobilized the detection antibody is added, forming a complex with the antigen. The detection antibody can be covalently linked to an enzyme, or can itself be detected by a secondary antibody which is linked to an enzyme through bioconjugation. Between each step the plate is typically washed with a mild detergent solution to remove any proteins or antibodies that are not specifically bound. After the final wash step the plate is developed by adding an enzymatic substrate to produce a visible signal, which indicates the quantity of antigen in the sample. Older ELISAs utilize chromogenic substrates, though newer assays employ fluorogenic substrates with much higher sensitivity.

DELFIA (dissociation enhanced lanthanide fluoro immuno assay)-based assays are solid phase assay. The antibody is usually labelled with Europium or another lanthanide and the Europium fluorescence is detected after having washed away un-bound Europium-labelled antibodies.

SPA (scintillation proximity assay) and the flashplate assay usually exploit biotin/avidin interactions for capturing radio labelled substrates. Generally the reaction mixture includes the kinase, a biotinylated peptide substrate and $\gamma$-[$^{33}$P]ATP. After the reaction, the biotinylated peptides are captured by streptavidin. In the SPA detection, streptavidin is bound on scintillant containing beads whereas in the flashplate detection, streptavidin is bound to the interior of the well of scintillant containing microplates. Once immobilized, the radiolabelled substrate is close enough to the scintillant to stimulate the emission of light.

Fluorescence resonance energy transfer (FRET) describes a radiation-free energy transfer between two chromophores. A donor chromophore in its excited state can transfer energy by a non-radiative long-range dipole-dipole coupling mechanism to an acceptor fluorophore in close proximity (typically <10 nm). As both molecules are fluorescent, the energy transfer is often referred to as "fluorescence resonance energy transfer", although the energy is not actually transferred by fluorescence. FRET is a useful tool to detect and quantify protein-agent interactions, protein-protein interactions, protein-DNA interactions, and protein-conformational changes. For monitoring binding of a protein to an agent, one protein to another or a protein to DNA, one of the molecules is labeled with a donor and the other with an acceptor and these fluorophore-labeled molecules are mixed. When they are present in an unbound state, donor emission is detected upon donor excitation. Upon binding of the molecules, the donor and acceptor are brought in proximity and the acceptor emission is predominantly observed because of the intermolecular FRET from the donor to the acceptor. Suitable neighbors for FRET are known in the art and the skilled practitioner will be able to choose a suitable combination of labels for both antibodies. As used herein with respect to donor and corresponding acceptor, "corresponding" refers to an acceptor fluorescent moiety having an emission spectrum that overlaps with the excitation spectrum of the donor. However, both signals should be separable from each other. Accordingly, the wavelength maximum of the emission spectrum of the acceptor should preferably be at least 30 nm, more preferably at least 50 nm, such as at least 80 nm, at least 100 nm or at least 150 nm greater than the wavelength maximum of the excitation spectrum of the donor (see also Example 3.1).

Representative donor fluorescent moieties that can be used with various acceptor fluorescent moieties in FRET technology include fluorescein, Lucifer Yellow, B-phycoerythrin, 9-acridineisothiocyanate, Lucifer Yellow VS, 4-acetamido-4'-isothiocyanatostilbene-2,2'-disulfonic acid, 7-diethylamino-3-(4'-isothiocyanatophenyl)-4-methylcoumarin, succinimdyl 1-pyrenebutyrate, and 4-acetamido-4'-isothiocyanatostilbene-2,2'-disulfonic acid derivatives.

Representative acceptor fluorescent moieties, depending upon the donor fluorescent moiety used, include LC-Red 610, LC-Red 640, LC-Red 670, LC-Red 705, Cy5, Cy5.5, Lissamine rhodamine B sulfonyl chloride, tetramethyl rhodamine isothiocyanate, rhodamine x isothiocyanate, erythrosine isothiocyanate, fluorescein, diethylenetriamine pentaacetate or other chelates of Lanthanide ions (e.g., Europium, or Terbium). Donor and acceptor fluorescent moieties can be obtained, for example, from Molecular Probes (Junction City, Oreg.) or Sigma Chemical Co. (St. Louis, Mo.).

Alternatively, time-resolved fluorescence resonance energy transfer (TR-FRET) may be used for the test system of the present invention. TR-FRET unites TRF (time-resolved fluorescence) and the FRET principle. This combination combines the low background benefits of TRF and the homogeneous assay format of FRET. While FRET has already been described above, TRF takes advantage of the unique properties of lanthanides or any other donor with long half-life. Suitable donors for TR-FRET include, amongst others, lanthanide chelates (cryptates) and some other metal ligand complexes, which can have fluorescent half-life in the micro- to millisecond time range and which, therefore, also allow the energy transfer to occur in micro- to millisecond measurements. Fluorescence lanthanide chelates have been used as energy donors in the late seventies. The commonly used lanthanides include samarium (Sm), europium (Eu), terbium (Tb) and dysprosium (Dy). Because of their specific photophysical and spectral properties, complexes of lanthanides are of major interest for fluorescence application in biology. Specifically, they have a large stroke's shift and extremely long emission half-lives (from microseconds to milliseconds) when compared to more traditional fluorophores.

Usually, organic chromophores are used as acceptors. These include allophycocyanin (APC). Suitable details on TR-FRET as well as acceptors are described in WO 98/15830.

Fluorescence polarisation (FP)-based assays are assays which use polarized light to excite fluorescent substrate peptides in solution. These fluorescent peptides are free in solution and tumble, causing the emitted light to become depolarised. When the substrate peptide binds to a larger molecule, its tumbling rates are greatly decreased, and the emitted light remains highly polarized (see also Example 4.3).

In a further embodiment of the invention, the test system of the invention is adapted for an amplified luminescence proximity homogeneous assay (ALPHA). ALPHA is a solution-based assay which was originally developed by Packard BioScience. ALPHA is a luminescence-based proximity assay, wherein one interaction partner is attached to donor beads, while the other is coupled to acceptor beads, both with a diameter of only about 250 nm. A photosensitizer compound is embedded into the donor bead. With this compound upon illumination with laser light at a wavelength of about 680 nm, ambient oxygen is converted into energy-rich, short-life singlet oxygen. When no acceptor bead is in proximity, the singlet oxygen decays without producing a signal. If donor and acceptor bead are brought together (ca. 250 nm) by the biological interaction of the attached biomolecules, the singlet oxygen released by the donor bead initiates a luminescence/fluorescence cascade in the nearby acceptor bead, leading to a highly amplified signal in the 520-620 nm range. The luminescence signal is detected in a suitable reader. For more details regarding ALPHA techniques, see Ullman et al., 1994, Proc. Natl. Acad. Sci., USA 91, 5426-5430.

EFC (enzyme fragment complementation)-based assays or equivalent assays can be used in particular for high-throughput screening of compounds. The EFC assay is based on an engineered β-galactosidase enzyme that consists of two fragments—the enzyme acceptor (EA) and the enzyme donor (ED). When the fragments are separated, there is no β-galactosidase activity, but when the fragments are together they associate (complement) to form active enzyme. The EFC assay utilizes an ED-analyte conjugate in which the analyte may be recognized by a specific binding protein, such as an antibody or receptor. In the absence of the specific binding protein, the ED-analyte conjugate is capable of complementing EA to form active β-galactosidase, producing a positive luminescent signal. If the ED-analyte conjugate is bound by a specific binding protein, complementation with EA is prevented, and there is no signal. If free analyte is provided (in a sample), it will compete with the ED-analyte conjugate for binding to the specific binding protein. Free analyte will release ED-analyte conjugate for complementation with EA, producing a signal dependent upon the amount of free analyte present in the sample.

Two-hybrid screening is a molecular biology technique used to discover protein-protein interactions by testing for physical interactions (such as binding) between two proteins. The premise behind the test is the activation of downstream reporter gene(s) by the binding of a transcription factor onto an upstream activating sequence. For the purposes of two-hybrid screening, the transcription factor is split into two separate fragments, called the binding domain (BD) and activating domain (AD). The BD is the domain responsible for binding to the UAS and the AD is the domain responsible for activation of transcription.

Co-immunoprecipitation can use for the identification of protein complexes by precipitating one protein believed to be in a complex, additional members of the complex are captured as well and can be identified. The protein complexes, once bound to the specific antibody, are removed from the bulk solution by capture with an antibody-binding protein attached to a solid support such as an agarose bead. These antibody-binding proteins (Protein A, Protein G, Protein L) were initially isolated from bacteria and recognize a wide variety of antibodies. Following the initial capture of a protein or protein complex, the solid support is washed several times to remove any proteins not specifically and tightly bound through the antibody. After washing, the precipitated protein(s) are eluted and analyzed using gel electrophoresis, mass spectrometry, western blotting, or any number of other methods for identifying constituents in the complex. Thus, co-immunoprecipitation is a standard method to assess protein-protein interaction. A suitable test system involving coimmunoprecipition is described in Example 1.

In another preferred embodiment of the invention the means for detecting the interaction between the first and second protein may be adapted to measure one or more components downstream of HEBP1 in the signal cascade. The measuring may include the determination of the concentration eNOS mRNA or eNOS protein or a reporter protein or mRNA. The concentration may be measured in response to a potential modulator as described above. Means and methods for determining concentrations of one or more nucleic acids or proteins are well known to the skilled person and include such involving RT-PCR, mass spectrometry or FRET (see also Examples).

Exemplary test systems and their use are described in Example 1 to 4.

Preferably, the method is adapted for high-through put screening. In this method a large number of compounds is screened against the agents in either cell-free or whole-cell assays. Typically, these screenings are carried out in 96 well plates using automated, robotic station based technologies or in higher-density array ("chip") formats.

In a particular embodiment of the present invention the test system of the invention further comprises
an eNOS promoter and/or
one or more transcription factor(s) for the eNOS promoter.

The eNOS promoter is the regulatory region of the eNOS gene that allows transcription of the gene. As with many other constitutive expressed genes, the eNOS promoter lacks a classical TATA box. However, a series of conserved cis elements for Sp1, Ets, GATA, NF-1, AP-1, shear stress and sterol could be identified. Known stimuli of eNOS transcription are for example sheer stress through flowing blood, hypoxia and agents such as estrogen and lysophosphatidylcholine. eNOS transcription may be reduced due to oxygenated lipoprotein of low density (oxLDL) and tumor necrosis factor α.

A schematic illustration of transcription factor binding sites in human eNOS genes is shown by Searles (Searles, 2006, Am. J. Physiol. Cell Physiol. 291:C803-C860). By detailed analysis of a proximal co-promoter of human eNOS gene, two positive regulatory domains (PRDI and II) were identified at positions −104/−95 and −144/−115, respectively, relative to the transcription start. Members of the Ets family, Sp1, variants of Sp3, MAZ and YY1 were identified as regulatory transcription factors within this region. Within PRDI and II, positive protein DNA and protein-protein interactions with respect to eNOS transcription could be detected indicating that eNOS transcription is regulated precisely by complex interaction of transcription factors. Furthermore, a GATA binding site is located at position −230/−227, which is important for basal eNOS transcription. In addition to thiese cis elements, a 269NT enhancer sequence, 4.9 kB upstream the transcription start, was identified, whose function is regulated by AP2-, MAZ-, Sp1- and Ets-related factors in nucleoprotein complexes. However, the transcription factors described above are mostly ubiquitous expressed proteins, which are not suitable for selective eNOS regulation or control.

Posttranscriptional eNOS may be regulated by cis acting RNA elements, calmodulin and intracellular $Ca^{2+}$ acting as an activator of NO synthesis. Furthermore, by allosteric binding of heatshock protein 90, induced for example by histamine, VEGF or sheer stress, eNOS may be activated as well. eNOS activity may be also modulated by phosphorylation of serine or threonine residues. The protein kinases involved are for example protein kinase A, protein kinase C, adenosine monophosphate-activated protein kinase, $Ca^{2+}$/CaM-dependent protein kinase and serine/threonine kinase AKT. Phosphorylation of Ser1177 may be induced by sheer stress, VEGF and estradiol and increase eNOS activity. However, phosphorylation of Thr497 affects a decrease of activity. Dephosphorylation processes are mediated by phosphatases PPA2 and PP1.

Furthermore, it was shown that eNOS activity may be negatively influenced by protein-protein interaction, e.g. through association of the C-terminal domain of G-protein-coupled receptors (e.g. bradykinine B2 receptor). In Yeast Two Hybrid Assays, a 34 kDA protein was identified and referred to as NOSIP (eNOS interacting protein). NOSIP binds to the oxygen domain of eNOS and promotes the translocation of enzyme from calveolae into intracellular regions, leading to reduced NO production. The oxygen domain of eNOS was used as bait in order to identify eNOS-interacting protein NOSTRIN (eNOS trafficking inducer). Overexpression of NOSTRIN lead to translocation of eNOS from plasma membrane to vascular structure and to reduced NO release. It could be shown that NOSTRIN forms a ternary complex with eNOS and caveolin-1. Furthermore, it is responsible for the recruitment of mediator proteins such as dynamine-2.

Human, bovine, murine and porcine eNOS promoters of endothelial cells have been cloned and show high sequence homology. The eNOS gene consists of 26 exons and encompasses approximately 21 kB genomic DNA on chromosome 7Q35-36. The 4052NT eNOS-mRNA is constitutively expressed in endothelial cells and very stable.

In addition to HEBP1 one or more transcription factor(s) for the eNOS promoter and/or one or more of the above factors required to effect transcription may be present.

The test system of the invention may comprise a cell, particularly a mammalian cell, especially a human cell. Examples of suitable cells include endothelial cells. These cells may be e.g. primary cells such as Human Umbilical Vein Endothelial Cell (HUVEC) (see Example 1) or a cell line such as EA.hy926 cells (see Example 1). However, any other cell or cell line, optionally genetically modified to include HEBP1 protein or components needed for detection of an effect, may be used.

In a preferred method of the present invention the effect is determined by fluorescence. Suitable methods are detailed above and may involve a fluorescence marker, FRET, fluorescence polarization, as detailed herein.

In another preferred embodiment of the invention, the method is used to screen for a medicament for preventing and/or treating a disease involving eNOS dysfunction, particularly a cardiovascular disease such as myocardial infarction and/or heart failure.

Exemplary diseases involving eNOS dysfunction are detailed above. However, cardiovascular diseases, especially myocardial infarction and/or heart failure are preferred. In accordance with the present invention the term "prevention of a disease" relates to the reduction of the risk of developing the prevailing disease, whereas the term "treatment of a disease" relates to the amelioration of the symptoms of the prevailing disease condition, deceleration of the course of disease etc. A prevention or preventive measure is a way to avoid an injury, sickness, or disease in the first place. A treatment or cure is applied after a medical problem has already started. A treatment treats a health problem, and may lead to its cure, but treatments more often ameliorate a problem only for as long as the treatment is continued. Cures are a subset of treatments that reverse illnesses completely or end medical problems permanently.

A further subject of the present invention relates to a method of diagnosing a cardiovascular disease in a subject, the method comprising
determining the level of HEBP1 mRNA or HEBP1 protein in a sample obtained from the subject,
wherein an increased or decreased level of HEBP1 mRNA or HEBP1 protein relative to a control is indicative of a cardiovascular disease.

As shown in the examples altered HEBP1 protein level is associated with cardiovascular disease, particularly heart failure and/or myocardial infarction. Accordingly, the level of HEBP1 mRNA or HEBP1 protein in a sample obtained from the subject may be determined in order to detect a level differing from a control level (e.g. from a healthy subject or determined at a group of healthy subjects), which is indicative of the above diseases.

The terms "sample from a subject" and "test sample" refer to all biological fluids and excretions isolated from any given subject, particularly a human. In the context of the present invention such samples include, but are not limited to, blood, blood serum, blood plasma, nipple aspirate, urine, semen, seminal fluid, seminal plasma, prostatic fluid, excreta, tears, saliva, sweat, biopsy, ascites, cerebrospinal fluid, milk, lymph, bronchial and other lavage samples, or tissue extract samples. Typically, blood or cardiovascular tissue samples are preferred test samples for use in the context of the present invention.

The level of HEBP1 mRNA or HEBP1 protein may be determined by a series of methods including those described herein, particularly also in the context of the screening method of the invention and in the examples.

Alternatively, mass spectrometry may be used. The term "mass spectrometry" refers to the use of an ionization source to generate gas phase ions from a sample on a surface and detecting the gas phase ions with a mass spectrometer. The term "laser desorption mass spectrometry" refers to the use of a laser as an ionization source to generate gas phase ions from a sample on a surface and detecting the gas phase ions with a mass spectrometer. A preferred method of mass spectrometry for biomolecules such as HEBP1 is matrix-assisted laser desorption/ionization mass spectrometry or MALDI. In MALDI, the analyte is typically mixed with a matrix material that, upon drying, co-crystallizes with the analyte. The matrix material absorbs energy from the energy source which otherwise would fragment the labile biomolecules or analytes. Another preferred method is surface-enhanced laser desorption/ionization mass spectrometry or SELDI. In SELDI, the surface on which the analyte is applied plays an active role in the analyte capture and/or desorption. In the context of the invention the sample comprises a biological sample that may have undergone chromatographic or other chemical processing and a suitable matrix substrate.

In mass spectrometry the "apparent molecular mass" refers to the molecular mass (in Daltons)-to-charge value, m/z, of the detected ions. How the apparent molecular mass is derived is dependent upon the type of mass spectrometer used. With a time-of-flight mass spectrometer, the apparent molecular mass is a function of the time from ionization to detection. The term "signal" refers to any response generated by a biomolecule under investigation. For example, the term signal refers to the response generated by a biomolecule hitting the detector of a mass spectrometer. The signal intensity correlates with the amount or concentration of the biomolecule. The signal is defined by two values: an apparent molecular mass value and an intensity value generated as described. The mass value is an elemental characteristic of the biomolecule, whereas the intensity value accords to a certain amount or concentration of the biomolecule with the corresponding apparent molecular mass value. Thus, the "signal" always refers to the properties of the biomolecule.

Alternatively, the presence and quantity of HEBP1 in the test sample can be obtained and quantified using routine techniques known to those skilled in the art. For example, methods for quantifying antigens or antibodies in test samples are well known to those skilled in the art. For example, the presence and quantification of HEPB1 in a test sample can be determined using an immunoassay. Immunoassays typically comprise: (a) providing an antibody (or antigen) that specifically binds to the biomarker; (b) contacting a test sample with the antibody or antigen; and (c) detecting the presence of a complex of the antibody bound to the antigen in the test sample or a complex of the antigen bound to the antibody in the test sample. An Exemplary antibody is described in the example. However, an alternative antibody may be produced in accordance with methods known by the skilled practitioner.

After the antibody is provided, HEBP1 can be detected and/or quantified using any of a number of well recognized immunological binding assays. Assays that can be used in the present invention include, for example, an enzyme linked immunosorbent assay (ELISA), which is also known as a "sandwich assay", an enzyme immunoassay (EIA), a radio-immunoassay (RIA), a fluoroimmunoassay (FIA), a chemiluminescent immunoassay (CLIA) a counting immunoassay (CIA), a filter media enzyme immunoassay (MEIA), a fluorescence-linked immunosorbent assay (FLISA), agglutination immunoassays and multiplex fluorescent immunoassays (such as the Luminex™ LabMAP), etc. For a review of the general immunoassays, see also, *Methods in Cell Biology Antibodies in Cell Biology*, volume 37 (Asai, ed. 1993); *Basic and Clinical Immunology* (Stites & Terr, eds., 7th ed. 1991).

Generally, a test sample obtained from a subject can be contacted with the antibody that specifically binds an antigen. Optionally, the antibody can be fixed to a solid support prior to contacting the antibody with a test sample to facilitate washing and subsequent isolation of the complex. Examples of solid supports include glass or plastic in the form of, for example, a microtiter plate, a glass microscope slide or cover slip, a stick, a bead, or a microbead.

After incubating the sample with antibodies, the mixture is washed and the antibody-antigen complex formed can be detected. This can be accomplished by incubating the washed mixture with a detection reagent. This detection reagent may be, for example, a second antibody which is labeled with a detectable label. In terms of the detectable label, any detectable label known in the art can be used. For example, the detectable label can be a radioactive label (such as, e.g., $^3$H, $^{125}$I, $^{35}$S, $^{14}$C, $^{32}$P, and $^{33}$P), an enzymatic label (such as, for example, horseradish peroxidase, alkaline phosphatase, glucose 6-phosphate dehydrogenase, and the like), a chemiluminescent label (such as, for example, acridinium esters, acridinium thioesters, acridinium sulfonamides, phenanthridinium esters, luminal, isoluminol and the like), a fluorescence label (such as, for example, fluorescein (for example, 5-fluorescein, 6-carboxyfluorescein, 3'6-carboxyfluorescein, 5(6)-carboxyfluorescein, 6-hexachloro-fluorescein, 6-tetrachlorofluorescein, fluorescein isothiocyanate, and the like)), rhodamine, phycobiliproteins, R-phycoerythrin, quantum dots (for example, zinc sulfide-capped cadmium selenide), a thermometric label, or an immuno-polymerase chain reaction label.

Throughout the assays, incubation and/or washing steps may be required after each combination of reagents. Incubation steps can vary from about 5 seconds to several hours, preferably from about 5 minutes to about 24 hours. However, the incubation time will depend upon the assay format, biomarker (antigen), volume of solution, concentrations and the like. Usually the assays will be carried out at ambient temperature, although they can be conducted over a range of temperatures, such as 10° C. to 40° C.

Preferably, the level of HEBP1 mRNA or HEBP1 protein in a sample obtained from the subject is decreased relative to the control.

The sample may be any sample suitable for the detection of an altered level of HEBP1 mRNA or HEBP1 protein. However, preferably the level is determined in a cardiovascular sample, such as an endothelial cell, particularly of the cardiovascular system, or a heart cell.

As detailed herein, eNOS dysfunction and HEBP1 alterations are particularly relevant for a cardiovascular disease. Preferably the cardiovascular disease is heart failure and/or myocardial infarction.

In accordance with the present invention HEBP1 may be used for the identification of a medicament for preventing and/or treating a disease involving eNOS dysfunction, particularly a cardiovascular disease. Therefore, a further subject of the invention relates to the use of HEBP-1 for the identification of a medicament for preventing and/or treating a disease involving eNOS dysfunction, particularly a cardiovascular disease.

However, endothelial dysfunction due to diminishing of nitric oxide in endothelial cells is one of the main mechanisms for vascular diseases, and often leading to atherosclerosis. This is very common in patients with diabetes mellitus, hypertension or other chronic pathophysiological conditions. Accordingly, the modulator may be used in the prevention or treatment of side effects of chronic pathophysiological conditions associated with endothelial dysfunction such as diabetes mellitus or hypertension.

Preferably, the medicament alters, preferably increases, expression of eNOS.

Also in accordance with the present invention, HEBP1 may be used for the detection of a component of eNOS signal transduction. Therefore, a still further subject of the invention relates to the use of HEBP-1 for the detection of a component of eNOS signal transduction. The detection of further components may be carried out using the methods described in the examples such as the use of HEBP1 as bait, protein microarrays, siRNAs, reporter systems, mass spectrometry, affinity purification, SDS PAGE, etc. (see particularly Examples 1 and 2, wherein HEBP1 is to be used as bait). In these methods, HEBP1 is preferably human HEBP1. HEBP1 can be used in order to detect binding partners and/or components of the upstream or downstream signal transduction not yet known. Depending on the component the methods described above in the context of the screening method of the invention may be used in order to quantify or detect effects of components to be detected.

Yet, another subject of the invention relates to the use of HEBP1 for the regulation of eNOS promoter activity. In accordance with the present invention HEBP1 may be used in order to regulate eNOS promoter activity. Regulation includes increase, promotion decrease, inhibition, and blockade of eNOS promoter activity. Regulation of eNOS promoter activity may be used in order to regulate eNOS expression in a cell, tissue or organ. Optionally, further components may be involved in the regulation such as compounds specifically regulating to HEBP-1 or the eNOS promoter such as AVE3085, AVE9488 or substance 9257 (see Examples). However, the eNOS promoter may be also operatively linked (e.g. by genetic engineering) to a different gene (e.g. a reporter gene or any other gene) in order to regulate the expression of that gene by eNOS promoter and HEBP1. This may be used in order to simulate eNOS expression in cardiovascular, particular endothelial, cells for research purposes, medical purposes or any other purpose. For example, this construct could be used in a model of cardiovascular diseases in order to study eNOS expression or eNOS promoter activity and its regulation. The eNOS promoter and HEBP1 may be used as inducible or tissue-specific promoter with basal activity as known by the skilled practitioner.

The invention is not limited to the particular methodology, protocols, and reagents described herein because they may vary. Further, the terminology used herein is for the purpose of describing particular embodiments only and is not intended to limit the scope of the present invention. As used herein and in the appended claims, the singular forms "a," "an," and "the" include plural reference unless the context clearly dictates otherwise. Similarly, the words "comprise", "contain" and "encompass" are to be interpreted inclusively rather than exclusively.

Unless defined otherwise, all technical and scientific terms and any acronyms used herein have the same meanings as commonly understood by one of ordinary skill in the art in the field of the invention. Although any methods and materials similar or equivalent to those described herein can be used in the practice of the present invention, the preferred methods, and materials are described herein.

The invention is further illustrated by the following figures and examples, although it will be understood that the figures and examples are included merely for purposes of illustration and are not intended to limit the scope of the invention unless otherwise specifically indicated.

FIGURES

FIG. 1 shows Validation of different HEBP1-siRNAs at the mRNA level. The relative HEBP1-expression, normalized to GAPDH, was determined 24 h after transfection of EA.csr03 cells (96-well format, n=4) with specific TaqMan®-probes by quantitative RT-PCR (* p<0.05 vs. siLV2-control). siRNA HEBP1 25 is capable of inhibiting HEBP1 gene transcription.

Figure 2:
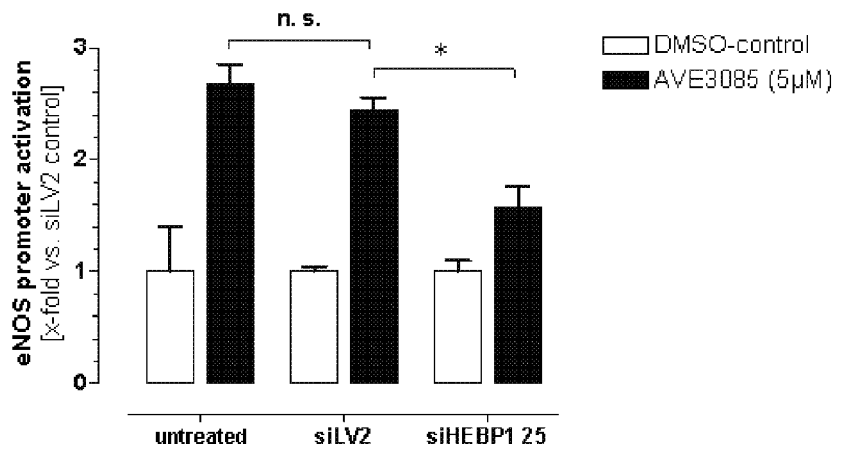

FIG. 2 shows Switching-off of HEBP1 using siRNA and subsequent measurement of promoter activation by AVE3085. This experiment was carried out in the 96-well format (n=4). The measured chemiluminescence was normalized to the total cellular protein content. siRNA HEBP1 25 is capable of inhibiting eNOS promoter activation.

Figure 3:
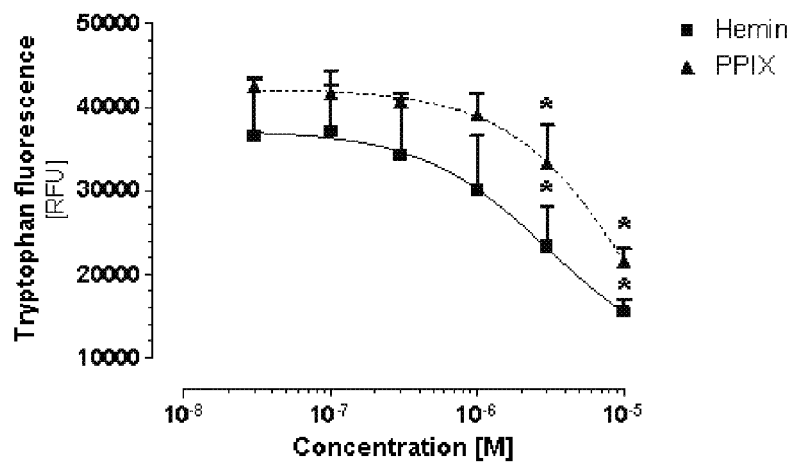

FIG. 3 shows Binding Studies of hemin and PPIX to human Hexahis-HEBP1 by tryptophan quenching. To a 0.5 μM HEBP1 solution heme and PPIX were added at concentrations of from 30 nM to 10 μM. After a 10 min incubation tryptophan fluorescence was measured ($\lambda_{ex}$=295 nm/$\lambda_{em}$=340 nm). Shown are means±SD of 6 experiments, * p<0.05 vs. 30 nM hemin/PPIX. Heme and PPIX are capable of quenching tryptophan fluorescence of human Hexahis-HEBP1 in a dose-dependent manner.

Figure 4:
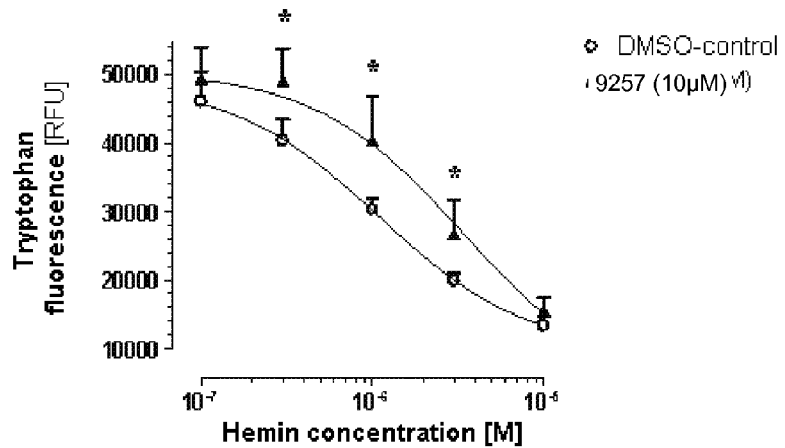

FIG. 4 shows Influence of the eNOS-transcription enhancer 9257 on the binding of hemin to 6×His-huHEBP1 from measurement of tryptophan quenching. A 0.5 μM HEBP1 solution was preincubated with 9257 (10 μM) at ice for 10 min. After addition of heme in different concentrations tryptophan fluorescence was measured ($\lambda_{ex}$=295 nm/$\lambda_{em}$=340 nm). Shown are means±SD of 6 experiments, * p<0.05 vs. DMSO control. 9257 influences the binding of heme to Hexahis-HEBP1.

Figure 5:
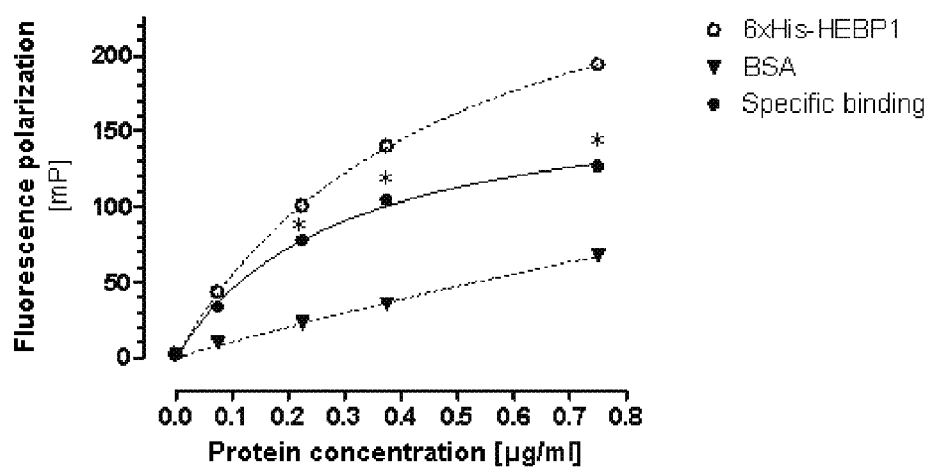

FIG. 5 shows Investigation of the specific binding of A300 to HEBP1 by fluorescence polarization measurement. Substance A300 (30 nM) was incubated with various concentrations of Hexahis-HEBP1 or BSA at room temperature for 10 min. Thereafter, fluorescence polarization was measured ($\lambda_{ex}$=530 nm/$\lambda_{em}$=585 nm). Means±SD of 5 experiments are shown, * p<0.05 vs. DMSO control without protein. eNOS substance A300 binds specifically to Hexahis-HEBP1.

Figure 6:
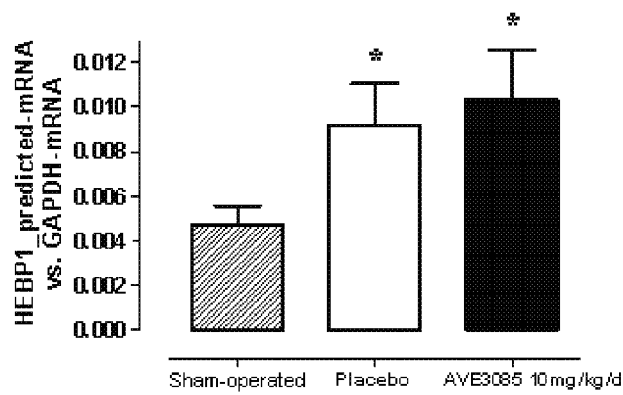

FIG. 6 shows Expression of HEBP1_predicted in cardiac tissue of rats with chronic heart failure after myocardial infarction. Rats were divided in three groups. One group was sham-operated (group 1), whereas in groups 2 and 3 chronic heart failure was induced by myocardial infarction. Only, the latter group was treated with AVE3085 (10 mg/(kg day)) for 9 weeks. Thereafter, mRNA expression (HEBP1 in comparison to GAPDH) was determined in heart tissue. Means±SD of 7 experiments are shown, * p<0.05 vs. sham operated. This experiment suggests that HEBP1 is involved I the pathogenesis of with chronic heart failure.

EXAMPLES

Example 1

Purification of Potential eNOS Targets Using Affinity Chromatography

The principle of affinity purification of potential target proteins proceeds in the manner wherein a pharmacophore, whose target protein is to be purified, is immobilized on a matrix by means of a chemical coupling (so-called linker). If protein lysates from cell cultures are added to the specific affinity material, the pharmacophore acts as a kind of "bait" and "fishes out" proteins with affinity for the pharmacophore. This method was used in the present work for purifying/amplifying target molecules. Specific column materials in active and inactive conformation of the pharmacophore were used (see below). $3 \times 10^7$ EA.csr03 cells (see below) were used for affinity chromatography and were stored as cell pellets at $-70°$ C. For lysis, the pellets were resuspended in a buffer of DPBS with 0.5% Tween 20 (1 ml/100 mg cell pellet) and were disrupted ultrasonically ($3 \times 30$ s, pulse 5, intensity 20%). Control of cell lysis was effected by microscopy. Cell debris was separated by two centrifugation steps (first 10 min at $1000 \times g/4°$ C., then 30 min at $70\,000 \times g/4°$ C.). The protein concentration in the supernatant was determined by the BCA method. Approx. 5 mg protein was obtained from $3 \times 10^7$.

Subsequent preparative affinity chromatography with the EA.csr03 cell lysates on specific, Sepharose-coupled column materials and identification of bound proteins by mass spectrometry were carried out. After several washing steps, the bound proteins were eluted by adding SDS and were separated using polyacrylamide-gel electrophoresis. After silver staining of the gel, the complete trace of all eluted proteins was cut up into approx. 60 pieces of gel. These were digested individually with trypsin to protein fragments, separated on a C18-column and identified using MS-MS/MS.

Denaturing polyacrylamide-gel electrophoresis (SDS-PAGE) is a method of gel electrophoresis by which various proteins can be separated according to their molecular weight. This possibility results from addition of the anionic surfactant sodium dodecylsulfate (SDS) to a protein mixture that is to be separated. The SDS attaches to the proteins and masks the intrinsic charge of the proteins. Negatively charged SDS-protein complexes are formed, with a constant charge-to-mass ratio of approx. 1.4 g SDS/g protein (~1 molecule SDS/3 amino acids). Through additional heating of the samples, secondary and tertiary structures of the proteins are disrupted. In addition, reducing agents, e.g. β-mercaptoethanol and DTT, are added to the samples to cleave disulfide bridges. The separating medium used in SDS-PAGE is a gelmatrix of polyacrylamide, which results from the crosslinking of acrylamide with methylenebisacrylamide. On applying an electric field, the SDS-protein complexes migrate through the separating matrix and are separated according to their size through the so-called "molecular sieve effect".

To generate different cell samples for gel electrophoresis, cells were washed carefully with DPBS ($37°$ C.) twice and are then lysed with 1×SDS sample buffer (50 mM Trizma Base (pH 6.8), 1.6% (w/v) SDS; 4% (w/v) glycerol, 0.01% (w/v) bromophenol blue, 5% (v/v) 13-mercaptoethanol, 325U Benzonase®, protease inhibitors and water to 10 ml). Then the enzyme Benzonase® was added and the samples were shaken for 15 min at $37°$ C. Benzonase® is a genetically engineered endonuclease, degrading RNA and DNA in the cell lysate, thus reducing the viscosity of the samples considerably and ensuring better separation of the protein mixture in electrophoresis. The protein samples were then denatured by heating at $70°$ C. for 20 min. The samples were either used directly in electrophoresis or were stored at $-20°$ C. until use. In the experiments on the phosphorylation status of the MAP kinases, in addition phosphatase inhibitors (Cocktail 1 and 2) in the ratio 1:100 were added to the DPBS and to the sample buffer. The Novex® Midi Gel System from Invitrogen (Karlsruhe, Germany) was employed for gel electrophoresis. With this ready-made gel system it is possible to apply up to 26 samples per gel. In addition, in the associated XCell4 SureLock™ Midi-Cell chamber up to four gels can be submitted to electrophoresis simultaneously. 4-12% Bis-Tris polyacrylamide gels with 26 sample pockets were used. They are so-called "gradient gels", i.e. the polyacrylamide concentration increases with increasing separation path and thus permits simultaneous separation of small and large proteins. In all the experiments, a suitable protein standard was also run for estimating the molecular weights of the proteins investigated. Depending on the required separation range, selection was made between an MES-SDS and a MOPS-SIDES running buffer. Additionally, 435 µl NuPAGE® antioxidant per gel was added to the running buffer of the upper chamber. Gel electrophoresis was then carried out at a constant voltage of 200V for 40 min with MES-SIDES running buffer and for 55 min with MOPS-SIDES running buffer.

For silver staining of protein gels, the coloration of proteins with silver solutions is based classically on the principle that $Ag^+$ ions form complexes with the glutamic-acid, aspartic-acid, and cysteine residues. Reduction of the $Ag^+$ ions gives elemental silver, producing a brownish coloration of the protein bands. The advantage of silver staining over other methods, e.g. Coomassie staining, resides in the high sensitivity of the method. Thus, even amounts of protein starting from 5 ng protein/0.5 cm band can be visualized, which is a considerable advantage especially for qualitative studies. For qualitative analysis of proteins in polyacrylamide gels, silver staining was carried out using the SilverSNAP® Stain Kits II from the company Pierce (Rockford, USA) following the manufacturer's standard instructions. The principle of this procedure is based on fixation of the proteins in the gel by means of an ethanolic acetic acid solution (30% (v/v) ethanol, 10% (v/v) acetic acid). This is followed by incubation with a silver salt solution and reduction of the silver ions to elemental silver, which stains the protein bands.

"Western blotting" means the transfer of proteins after separation in gel electrophoresis to a polymer support layer. In this way the proteins are made more easily accessible for antibodies in subsequent immunodetection. Basically, various polymers are suitable as support materials, e.g. nylon, PVDF and nitrocellulose. An electric voltage applied perpendicularly to the gel and the membrane causes the proteins to migrate from the gel to the membrane. The pattern of bands of the preceding separation is retained in this process. In the blotting method that was used, with nitrocellulose as support material, the binding of the proteins to the membrane is based on hydrophobic. To prepare a gel for blotting after gel electrophoresis, it was equilibrated for 20 min in a 2× transfer buffer (50 ml 20× NuPAGE® transfer buffer, 50 ml methanol, 500 µl NuPAGE® antioxidant and water to 500 ml). The nitrocellulose membrane was washed briefly with water and incubated together with six filter papers per gel in 2× transfer buffer. The transfer itself was carried out in a "Semi-Dry-Blotter" (Biostep, Jahnsdorf, Germany). The gel and the membrane were embedded between impregnated filter papers above and below on the "sandwich principle" and a constant voltage of 20V was applied for 60 min.

In previous studies, two small-molecular-weight compounds with related structures enhanced eNOS promoter activity in a concentration-dependent manner:

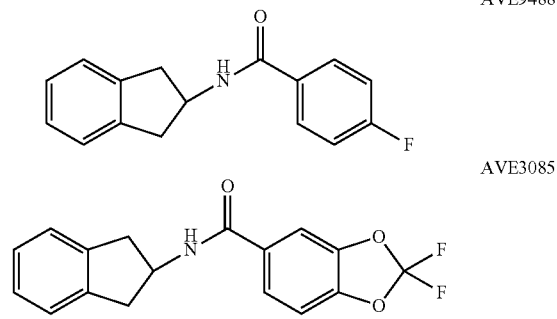

AVE9488: 4-fluoro-N-indan-2-yl-benzamide; CAS NO: 291756-32-6)
AVE3085: 2,2-difluoro-benzo[1,3]dioxole-5-carboxylic acid indan-2-ylamide; CAS NO.: 450348-85-3)

AVE3085 was used as "bait" for the identification potential targets. Four different column materials for the enrichment of potential targets were synthesized using affinity chromatography (Table 1). For synthesis, the pharmacophore was reacted with N-hydroxysuccinimide ester (NHS)-activated Sepharose and was bound covalently through formation of an ether bridge. Binding sites of the NHS-Sepharose that had not been saturated were saturated by reaction with ethanolamine.

Substance A095 is column material without a pharmacophore as "bait" on the linker. The purpose of this control is to identify and rule out proteins that bind nonspecifically to the column material, in the list of potential target molecules.

In the other column materials the pharmacophore is coupled covalently via the linker to the Sepharose particles. Thus, substance A093 is a material in which the pharmacophore is coupled to the matrix via a linker with three polyamide linkages. In the case of materials A092 and A094, this linker is somewhat longer as it has an additional ether linkage. Moreover, the pharmacophore was in the active conformation in substance A092, and in the inactive conformation in A094.

Affinity purifications of potential target proteins from whole cell lysates of EA.csr03 cells were carried out with all four column materials and the proteins thus enriched were identified, after trypsinolysis, by means of mass spectrometry. In addition, however, expression in EA.hy926 cells and HUVECs was also determined.

The EA.csr03 cells are cells of a stable eNOS-promoter luciferase cell line. It was obtained by transfection of EA.hy926 cells with a firefly luciferase reporter construct, with a 3.5 kb fragment of the eNOS-promoter added. Cultivation of these cells was carried out with IMDM with GlutaMAX™ I supplemented with 100 U/ml penicillin, 100 µg/ml streptomycin, 10% FCS and 0.4 mg/ml geneticin as selection antibiotic. The EA.hy926 cells are a stable human cell line, which was obtained by fusion of HUVEC with the human hybridoma cell line A549. This cell line is characterized by expression of specific endothelial cell markers, e.g.

TABLE 1

Affinity materials for the enrichment of potential targets of the eNOS-transcription enhancers from cell lysates

| Substance | Structural formula |
|---|---|
| A095 control | |
| A093 active | |
| A092 active | |
| A094 inactive | |

The symbol ● denotes a Sepharose particle the "van-Willebrand factor". The cells used are an original culture of Cora Jean Edgell of passage 32. The cells were cultivated in IMDM with GlutaMAX™ I supplemented with 100 U/ml penicillin, 100 µg/ml streptomycin, HAT Hybri-Max™ medium additive (hypoxanthine, aminopterin and thymidine) and Biotect protective medium.

The list of potential target molecules includes the proteins
 that were identified unambiguously with at least four protein fragments;
 that had not bound to the column material, without any pharmacophore being offered as "bait";
 that had bound preferentially to the column materials with the pharmacophore in active conformation.

Table 2 shows a consolidated list of the potential targets thus obtained. This table shows, for each protein identified, the unique accession number of the UniProtKB/Swiss-Prot databanks, the theoretical molecular weight and the number of protein fragments with which it was identified.

TABLE 2

Potential targets of the eNOS-transcription enhancers identified by affinity chromatography followed by mass spectrometry

| Databank number | Protein (gene symbol) | Molecular weight [kDa] | Number of protein fragments |
|---|---|---|---|
| O00625 | Pirin (PIR) | 32.1 | 5 |
| O00764 | Pyridoxal kinase (PDXK) | 35.1 | 10 |
| O75127 | Pentatricopeptide repeat protein 1 (PTCD1) | 78.8 | 8 |
| P17931 | Galectin-3 (LGALS3) | 26.0 | 7 |
| P27361 | Mitogen-activated protein kinase 3 (MAPK3) | 43.1 | 8 |
| P50213 | Isocitrate dehydrogenase [NAD], alpha subunit, mitochondrial precursor (IDH3A) | 39.6 | 15 |
| P55263 | Adenosine kinase (ADK) | 40.5 | 7 |
| P57721 | Poly(rC)-binding protein 3 (PCBP3) | 35.9 | 6 |
| P67775 | Serine/threonine-phosphatase 2A, catalytic subunit of the alpha-isoform (PPP2CA) | 35.6 | 6 |
| Q04760 | Lactoyl glutathionelyase (GLO1) | 20.6 | 9 |
| Q9BUP3 | Oxidoreductase HTATIP2 (HTATIP2) | 27.1 | 10 |
| Q9NRV9 | Heme-binding protein 1 (HEBP1) | 21.1 | 18 (vs. 2) |

Apart from the heme-binding protein 1 (HEBP1), the proteins listed are proteins that had bound exclusively to the active conformation of the column material. HEBP1 had also bound, as a single protein, to the inactive conformation of the column material. In this experiment, however, it could only be identified with two protein fragments versus 18 on the active conformation.

Example 2

Identifying Potential Target Proteins Using Protein Microarrays

The protein-microarray experiments were carried out using ProtoArrays® v3.0 (Invitrogen, Karlsruhe, Germany). These were nitrocellulose-coated glass plates, on which approx. 5000 recombinant human proteins, in duplicates, were immobilized.

For investigating the affinities of eNOS compounds using said microarrays, biotin-labeled eNOS transcription enhancers A012 (active conformation) and A012 (inactive conformation) were used and the binding of these substances to proteins was detected and quantified by fluorescence measurement using IRDye®680-labeled streptavidin.

In the first step the microarrays were incubated for one hour at 4° C. with a MOPS blocking buffer with 0.1% (v/v) Igepal and 1% (w/v) BSA. Then the arrays with the biotin-labeled eNOS transcription enhancers A012 and A013, sometimes in the presence of the unlabeled substance 9257, were incubated at 4° C. for 90 min without shaking, in various test conditions in a MOPS sample buffer with 1% (v/v) Igepal and 1% (w/v) BSA.

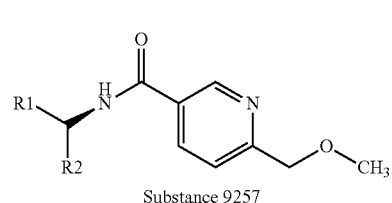

Substance 9257

After washing three times, in each case for 1 min, with pure MOPS sample buffer on ice, they were incubated for 30 min with IRDye®680-labeled streptavidin diluted 1/1000 in MOPS sample buffer away from the light, also on ice. IRDye®680- and IRDye®800-labeled secondary antibodies, which recognize the constant $F_c$-part of the primary antibodies, were used exclusively for the immunodetection of certain proteins. The fluorescence labeling used here possesses the property of emitting in the near infrared (wavelengths of $\lambda=700$-800 nm) after excitation with laser light. The advantage of this wavelength range is the very good signal-to-noise ratio on account of low intrinsic fluorescence. Detection employs the ODYSSEY™ from LI-COR Biosciences (Bad Homburg, Germany). With this instrument it is possible to detect both emission wavelengths on one membrane simultaneously. Through the simultaneous detection of target and reference protein, the normalization of individual samples is possible in just one step. Three further washing steps (each 1 min) with 0.1% (v/v) Igepal in PBS were followed by detection with ODYSSEY™ (LI-COR Biosciences, Bad Homburg, Germany).

After transfer, the membrane was blocked for one hour in ODYSSEY blocking buffer, diluted 1:1 with PBS. The purpose of this step is to saturate any remaining free protein binding sites on the membrane and so prevent nonspecific antibody binding. The membrane was incubated overnight at 4° C. with 1-2 primary antibodies in antibody-binding buffer (ODYSSEY blocking buffer (diluted 1:1 with PBS), 0.25% (v/v) Tween 20, 0.02% (w/v) sodium azide). Washing of the membranes (4×5 min) with PBST (PBS with 0.1% Tween 20) to remove unbound antibody was followed by incubation with the secondary antibodies. After incubation for one hour with the secondary antibodies in antibody-binding buffer (protected from the light, at room temperature) the membrane was washed again 4×5 min with PBST, followed by detection.

In order to be able to investigate the affinity of eNOS compounds using these microarrays, these compounds had either to be labeled directly, or it had to be possible to label them indirectly. In our experiments biotin-labeled eNOS-transcription enhancers were used in an active (A012) and inactive conformation (A013) (Table 3). These can be detected from fluorescence through high-affinity binding of IRDye®680-labeled streptavidin to the biotin residues of the substances.

TABLE 3

Structural formulas of biotin-labeled eNOS-transcription enhancers for use in the protein-microarray experiments Substance  Structural formula A012 active A013 inactive So as to be able to use the biotin-labeled eNOS substances A012 and A013 in the protein-microarray experiments, it was necessary to ensure that the biotin residue does not disturb the action of the pharmacophore and that there is sufficient activity. Cellular verification of the substances in the eNOS-transcription test was carried out for this purpose. Comparing substance A012 with the reference substance AVE9488, it is evident that despite the introduction of a linker with biotin labeling, A012 ($EC_{50}$=1.2 μM) is even slightly more active cellularly than the reference AVE9488 ($EC_{50}$=3.0 μM). The biotin-labeled substance A013 (inactive conformation) now had hardly any significant cellular activity (Cellular $EC_{50}$>10 μM). Thus, the two substances A012 and A013 were suitable for use in the protein-microarray labeling experiments.

In the protein-microarray experiment, one array in each case was incubated in three different conditions: A active, biotin-labeled eNOS-substance A012 (100 μM), B A012 (100 μM) in the presence of active, unlabeled substance 9257 (25 μM), and C inactive biotin-labeled substance A013 (100 μM).

The labeling of three different protein duplicates (A: numbers 1-3) with the active biotin-labeled substance A012 was readily discernible. Examination of the relevant competition experiment with substance 9257 (B) shows that the binding of A012 was markedly weaker, as it had been displaced by 9257 from binding. When a microarray was incubated with the inactive, biotin-labeled substance A013 there was no binding of the substance to the proteins (C) that had previously been labeled with the active biotin-substance.

These labeling (A) and competition tests (B) were evaluated by quantifying the fluorescence signals. Proteins for which competition could be demonstrated were included in a list as potential targets (Table 4):

TABLE 4

Potential target proteins from the protein-microarray experiments

| Databank number | Protein (gene symbol) | Fluorescence intensity A | Fluorescence intensity B |
|---|---|---|---|
| BC000381.2 | TBP-related Protein 1 (TBPL1) | 10788 | 4083 |
| BC016609.1 | Cytidinemonophosphate-N-acetylneuraminic acid-synthetase (CMAS) | 10411 | 5028 |

TABLE 4-continued

Potential target proteins from the protein-microarray experiments

| Databank number | Protein (gene symbol) | Fluorescence intensity A | Fluorescence intensity B |
|---|---|---|---|
| NM_007162.1 | Transcription factor EB (TFEB) | 4987 | 1333 |
| NM_002749.2 | Mitogen-activated protein kinase 7 (MAPK7) | 4775 | 1135 |
| NM_006251.4 | AMP-activated protein kinase, catalytic subunit alpha 1 (PRKAA1) | 3791 | 1206 |
| BC016645.2 | Phosphoserine aminotransferase 1 (PSAT1) | 3151 | 2269 |

As the proteins investigated were produced exclusively by recombinant techniques, it was not possible to verify their functionality. As these proteins were identified exclusively from binding affinities, they require functional validation as possible target proteins.

Example 3

Validation of Potential Targets from Affinity Chromatography and Protein-Microarray Experiments 1. Expression Profile of Potential Targets from Affinity Chromatography in Endothelial Cells A comprehensive expression profile of all potential targets was constructed at the mRNA level in various types of endothelial cells, to permit better assessment of the relevance of the proteins enriched in affinity chromatography. This investigation was based on the idea that the enrichment of poorly expressed proteins on the column material might indicate higher binding specificity in comparison with proteins, which are present in large quantity in the cells. For this purpose the expression of all potential target proteins was determined using quantitative RT-PCR and specific TaqMan®-probes.

Overview of TaqMan probes

| Gene symbol | Context sequence of the probe | SEQ ID NO: | Catalog No. |
| --- | --- | --- | --- |
| ADK | GGTGACAACAGGTCCCTCATAGCTA | 1 | Hs00417073_m1 |
| CMAS | TCAGAAAGGAGTTCGTGAAGTGACC | 2 | Hs00218814_m1 |
| GAPDH | GGCGCCTGGTCACCAGGGCTGCTTT | 3 | Hs99999905_m1 |
| Gapdh | Not available | | Rn99999916_s1 |
| GATA2 | CTCGTTCCTGTTCAGAAGGCCGGGA | 4 | Hs00231119_m1 |
| GLO1 | CACTTGAGCTGACACACAATTGGGG | 5 | Hs00198702_m1 |
| HEBP1 | TGTCTATTCCATGCAGTTTGGTGGT | 6 | Hs00211123_m1 |
| HEBP1_predicted | Not available | | Rn01459705_m1 |
| HTATIP2 | GGAAAGCTGGGGCGGAGGGATTTGT | 7 | Hs00185131_m1 |
| IDH3A | TAAGGACGGAAAGAGCTTGACAAAA | 8 | Hs00194253_m1 |
| IFIT1 | Not available | | Hs00356631_g1 |
| LGALS3 | CCCCTGCTGGGCCACTGATTGTGCC | 9 | Hs00173587_m1 |
| MAPK1 | GCATGGTGTGCTCTGCTTATGATAA | 10 | Hs00177066_m1 |
| MAPK3 | ATGAGAGATGTCTACATTGTGCAGG | 11 | Hs00177127_m1 |
| MAPK7 | TCAAATCTGTCTACGTGGTCCTGGA | 12 | Hs00177079_m1 |
| NOS3 | GAATGGAGAGAGCTTTGCAGCTGCC | 13 | Hs00167166_m1 |
| OAS1 | Not available | | Hs00242943_m1 |
| PCBP3 | GTATCTCATCAACGCCAGGCTGACG | 14 | Hs00608649_m1 |
| PDXK | AACCTCAAGGTGGCCTGTGAGAAGA | 15 | Hs00177600_m1 |
| PIR | CCCAGGAGATTTGCAGTGGATGACT | 16 | Hs00186374_m1 |
| PPP2CA | GAAGTTCCCCATGAGGGTCCAATGT | 17 | Hs00427259_m1 |
| PRKAA1 | ATGGAAGGCTGGATGAAAAAGAAAG | 18 | Hs00178893_m1 |
| PSAT1 | GTGCGGGAATTGCTAGCTGTTCCAG | 19 | Hs00795278_mH |
| PTCD1 | CGGTACGCCCTCCAGGTGTGGCGGC | 20 | Hs00248918_m1 |
| SP1 | GCAAATGCCCCAGGTGATCATGGAG | 21 | Hs00412720_m1 |
| TBPL1 | TTATAAACGTGATGTTGGAAAAGTA | 22 | Hs00191595_m1 |
| TFEB | TGCCCAACACGCTACCCCTGTCCAG | 23 | Hs00292981_m1 |

TaqMan probes were obtained from Applied Biosystems (Darmstadt, Germany). The supplier indicated the sequence to which the probe hybridizes, but not the sequences of the primers enclosed.

In quantitative reverse transcriptase PCR in real time (quantitative RT-PCR), reverse transcription and real-time PCR are carried out successively in a reaction setup. An enzyme mixture of two reverse transcriptases (Omniscript/Sensiscript Reverse Transcriptase) and the HOTStarTaq DNA polymerase were added to this. At the start of the reaction, the DNA polymerase is still in an inactive form and only reverse transcription of the mRNA to cDNA takes place at 50° C. Then the reverse transcriptases are inactivated and the DNA polymerase is heat-activated at 95° C. followed by cDNA amplification steps.

The cDNA amplified in real time is quantified by means of a sequence-specific primer pair and a fluorescence-labeled oligonucleotide probe, the so-called TaqMan® probe. This attaches to the DNA during the amplification between the two primers. The TaqMan® probe is labeled at one end with a fluorescent dye, and at the other end with a quencher. Fluorescence cannot be detected on the basis of fluorescence resonance energy transfer (FRET) at the start of the PCR. However, if during amplification the Taq polymerase comes close to the probe, this displays 5'→3' exonuclease activity at the double strand. The probe is cleaved, as a result of which the fluorophore is separated from the quencher. This process results in a detectable fluorescence, which increases in proportion to the PCR product formed.

A typical 20 µl reaction setup in the 96-well format generally consisted of 10 µl 2× Quantitect RT Mastermix, 1 µl 20× Assay Mix (primer and TaqMan probe from Applied Biosystems), 0.2 µl RT-mix, 5 µl RNA and 3.8 µl nuclease-free water. The reactions were carried out in the PCR detection system iCycler® from BioRad-Laboratories (Munich, Germany) according to the following amplification protocol:

| Temperature | Time | Step |
| --- | --- | --- |
| 50° C. | 40 min | Reverse transcription |
| 95° C. | 14 min | PCR-activation step |
| 94° C. | 15 s | 2-step amplification (45x) |
| 60° C. | 1 min | |
| 4° C. | unlimited | storage |

Quantification of a target mRNA was carried out by normalization to the amount of mRNA of the unregulated gene GAPDH ("housekeeping gene") and calculation by the ΔΔct method. This method is based on calculation of a fluorescence threshold value (ct) relative to a background fluorescence at the starting time, when there is still no PCR product present. The relative expression of a defined target gene versus an unstimulated control normalized to GAPDH is therefore calculated as follows:

$$\Delta ct = ct_{target\ gene} - ct_{GAPDH}$$

$$\Delta\Delta ct = ct_{sample} - ct_{control}$$

$$2^{-\Delta\Delta ct} = x\text{-fold expression}$$

The cell samples used were primarily RNA preparations from untreated EA.csr03 cells, lysates of which had also been used in affinity chromatography. The expression profile was compared to that of EA.hy926 and primary HUVECs. Primary human umbilical cord endothelial cells (HUVEC) were freshly prepared for each experiment by standard methods and were only used up to passage 3. The growth medium of these cells consisted of IMDM with GlutaMAX™ I, which was supplemented with 100 U/ml penicillin, 100 µg/ml streptomycin and 20% FCS. Cultivation was carried out on Collagen I-coated cell culture materials at 37° C. and 5% $CO_2$.

The expressions found for the potential targets were put in three categories (Table 5).

TABLE 5

Expression profile of potential targets from affinity chromatography

| Potential target | Gene symbol | EA.csr03 | EA.hy926 | HUVEC |
| --- | --- | --- | --- | --- |
| Pirin | PIR | medium | low | high |
| Pyridoxal kinase | PDXK | medium | medium | medium |
| Pentatricopeptide repeat protein | PTCD1 | low | low | low |
| Galectin-3 | LGALS3 | medium | medium | medium |
| Mitogen-activated protein kinase 3 | MAPK3 | medium | low | high |
| Isocitratedehydrogenase [NAD], subunit alpha, mitochondrial precursor | IDH3A | high | high | high |
| Adenosine kinase | ADK | medium | medium | medium |
| Poly(rC)-binding protein 3 | PCBP3 | low | low | low |
| Serine/threonine-protein phosphatase | PPP2CA | high | high | high |
| Lactoyl glutathionelyase | GLO1 | high | high | high |
| Oxidoreductase HTATIP2 | HTATIP2 | high | high | high |
| Heme-binding protein 1 | HEBP1 | high | high | high |

Classification in the three different categories was based on the expression of individual targets in comparison with GAPDH: high expression >0.015, medium expression of 0.005-0.015 and low expression <0.005.

With respect to the EA.csr03 cell line used in chromatography, high expression was found for the IDH3A, PPP2CA, GLO1, HTATIP2 and HEBP1 genes investigated. Medium expression levels were also noted for PIR, PDXK, LGALS3, MAPK3 and ADK, and very low expression was only obtained for PTCD1 and PCBP3.

If we compare the expression levels of individual genes between reporter cell line EA.csr03, its parent cell line EA.hy926 and primary HUVECs, generally no differences are found. It is only for PIR and MAPK3 that lower expression is found in the cell lines compared with the primary HUVECs.

2. Expression Profile of Potential Target Proteins from Protein-Microarray Experiments in Endothelial Cells The proteins on the protein-microarrays (see above) were exclusively recombinant proteins. Therefore it was important to verify which of them are expressed in endothelial cells. For this purpose the relative expression of the potential targets was determined by quantitative RT-PCR relative to GAPDH in RNA preparations from untreated EA.csr03 cells, EA.hy926 cells and primary HUVECs. The results are presented in Table 6.

TABLE 6

Expression profile of potential targets from the protein-microarray experiments

| Potential target | Gene symbol | EA.csr03 | EA.hy926 | HUVEC |
| --- | --- | --- | --- | --- |
| TBP1-like 1 | TBPL1 | low | low | low |
| Cytidine monophosphate N-actylneuraminic acid synthetase | CMAS | high | high | high |
| Transcription factor EB | TFEB | low | low | low |
| Mitogen-activated protein kinase 7 | MAPK7 | low | low | low |
| AMP-activated protein kinase, catalytic subunit alpha 1 | PRKAA1 | medium | medium | medium |
| Phosphoserine aminotransferase 1 | PSAT1 | low | high | low |

Classification in the three different categories was based on the expression of individual targets in comparison with GAPDH: high expression >0.015, medium expression of 0.005-0.015 and low expression <0.005.

Expression of most of the potential targets was low in the types of endothelial cells investigated (TBPL1, TFEB, MAPK7, PSAT1). Medium expression was only found for PRKAA1, and high expression for CMAS.

In this experiment, apart from one exception (PSAT1), there were no differences in the expression levels of individual targets between the cell lines and primary HUVECs.

3. Validation of Potential Targets Using the siRNA Technology

Affinity chromatography and protein-microarray experiments produced a consolidated list of a total of 18 potential target proteins. Identification of these proteins was based on affinity for various eNOS transcription enhancers in cell-free systems. For this reason all candidates underwent further cellular validation.

RNA interference (RNAi) means the sequence-specific, posttranscriptional suppression of some genes in animals and plants, which is initiated by double-stranded RNA (dsRNA) that is homologous to the target gene. In Caenorhabditis elegans and Drosophila melanogaster, the breakdown of long, sequence-specific dsRNA by the cytoplasmic, RNase III-like protein "Dicer" could be identified as the mechanism on which RNAi is based. There is formation of short fragments with a length of 19-25 nt, the so-called "small interfering RNAs (siRNAs). The resultant siRNAs are then incorporated in RNA-protein complexes called "RNA-induced silencing complex" (RISC) and serve as mediators of the subsequent RNA degradation. Separation of the two siRNA strands produces activation of the RISC. The activated complex can now bind to the homologous mRNA and cut it approx. 12 nucleotides away from the 3'-end of the siRNA.

In the present work, RNAi technology represented a key technique for validating the influence of potential target molecules of the eNOS transcription enhancers on the eNOS-promoter. Transfer of the siRNA molecules employed cationic, liposomal formulations, Lipofectin® for HUVECs and Lipofectamine™ 2000 for EA.hy926 or EA.csr03. These possess the property of complexing negatively charged nucleic acids on their positively charged surface. Owing to the lipidlike nature of the liposomes, these are able to interact with the cell membrane and transfer the complexed nucleic acids into the cell.

For liposomal transfection of siRNA in endothelial cells, EA.hy926 or EA.csr03 cells were sown with a density of 50 000 cells per well in a volume of 100 μl growth medium in 96-well plates. After incubation for 24 h in an incubator, the cells were washed with sterile DPBS and were covered in each case with 100 μl/well of serum-free and antibiotic-free special medium Opti-MEM® I. Then the siRNAs (see below) used were preincubated with Lipofectamine™ 2000 in accordance with the manufacturer's instructions and finally 50 μl/well of the transfection mixture was added to the cells. Unless stated otherwise, the siRNAs were used at final concentrations of 100 nM. Per well, after previous optimization, 0.8 μl of Lipofectamine™ 2000 was used for transfection of the EA.hy926 cells, and 0.5 μl for the EA.csr03 cells. After the cells had been incubated in an incubator for 6 hours, the transfection medium was replaced with normal growth medium and the next experimental steps were carried out in the time frame of 24-72 hours after transfection. Primary HUVECs were sown at 100 000 cells per well in Collagen I-coated 6-well plates and were cultivated in normal growth medium up to 60-70% confluence. Prior to transfection, the cells were washed with sterile DPBS and covered in each case with 800 μl/well of serum-free and antibiotic-free special medium Opti-MEM® I. 6 μl Lipofectin® and siRNA at a final concentration of 100 nM were used per well. Preincubation of siRNA and Lipofectin® was carried out in accordance with the manufacturer's instructions for HUVECs. After addition of 200 μl/well of the transfection formulation to the cells, incubation was carried out in an incubator for 6 hours. Then the transfection medium was replaced with normal growth medium. The subsequent experimental steps were carried out between 24 and 72 hours after transfection.

Overview of siRNAs

| Gene symbol + siRNA No. | Catalog No. | Manufacturer |
| --- | --- | --- |
| siADK 58 | Silencer ® siRNA, ID #1658 | Applied Bio Systems (Darmstadt) |
| siADK 68 | Silencer ® siRNA, ID #1568 | Applied Bio Systems (Darmstadt) |
| siADK 74 | Silencer ® siRNA, ID #1474 | Applied Bio Systems (Darmstadt) |
| siCMAS 01 | Silencer ® siRNA, ID #27201 | Applied Bio Systems (Darmstadt) |
| siCMAS 50 | Silencer ® siRNA, ID #119350 | Applied Bio Systems (Darmstadt) |
| siCMAS 91 | Silencer ® siRNA, ID #117991 | Applied Bio Systems (Darmstadt) |
| siETS1 23 | Silencer ® siRNA, ID #115623 | Applied Bio Systems (Darmstadt) |
| siETS1 24 | Silencer ® siRNA, ID #115624 | Applied Bio Systems (Darmstadt) |
| siETS1 30 | Silencer ® siRNA, ID #2830 | Applied Bio Systems (Darmstadt) |
| siGATA2 17 | Silencer ® siRNA, ID #145417 | Applied Bio Systems (Darmstadt) |
| siGATA2 18 | Silencer ® siRNA, ID #145418 | Applied Bio Systems (Darmstadt) |
| siGATA2 19 | Silencer ® siRNA, ID #145419 | Applied Bio Systems (Darmstadt) |
| siGLO1 13 | Silencer ® siRNA, ID #121613 | Applied Bio Systems (Darmstadt) |
| siGLO1 14 | Silencer ® siRNA, ID #121614 | Applied Bio Systems (Darmstadt) |
| siGLO1 15 | Silencer ® siRNA, ID #121615 | Applied Bio Systems (Darmstadt) |
| siHEBP1 12 | Silencer ® siRNA, ID #23712 | Applied Bio Systems (Darmstadt) |
| siHEBP1 20 | Silencer ® siRNA, ID #23620 | Applied Bio Systems (Darmstadt) |
| siHEBP1 25 | Silencer ® siRNA, ID #23525 | Applied Bio Systems (Darmstadt) |
| siHTATIP2 72 | Silencer ® siRNA, ID #135772 | Applied Bio Systems (Darmstadt) |
| siHTATIP2 73 | Silencer ® siRNA, ID #135773 | Applied Bio Systems (Darmstadt) |
| siHTATIP2 74 | Silencer ® siRNA, ID #135774 | Applied Bio Systems (Darmstadt) |
| SNDH3A 09 | Silencer ® siRNA, ID #16309 | Applied Bio Systems (Darmstadt) |
| siIDH3A 44 | Silencer ® siRNA, ID #107744 | Applied Bio Systems (Darmstadt) |
| siIDH3A 45 | Silencer ® siRNA, ID #107745 | Applied Bio Systems (Darmstadt) |
| siLGALS3 93 | Silencer ® siRNA, ID #279193 | Applied Bio Systems (Darmstadt) |
| siMAPK1 09 | SI00300748 | Qiagen (Hilden, Germany) |
| siMAPK1 10 | SI00300755 | Qiagen (Hilden, Germany) |
| siMAPK1 12 | SI00605983 | Qiagen (Hilden, Germany) |
| siMAPK1 13 | SI00605990 | Qiagen (Hilden, Germany) |
| siMAPK3 04 | Silencer ® siRNA, ID #142304 | Applied Bio Systems (Darmstadt) |
| siMAPK3 05 | Silencer ® siRNA, ID #142305 | Applied Bio Systems (Darmstadt) |
| siMAPK3 20 | Silencer ® siRNA, ID #202320 | Applied Bio Systems (Darmstadt) |
| siMAPK7 14 | Silencer ® siRNA, ID #1414 | Applied Bio Systems (Darmstadt) |
| siMAPK7 87 | Silencer ® siRNA, ID #110787 | Applied Bio Systems (Darmstadt) |
| siMAPK7 92 | Silencer ® siRNA, ID #110792 | Applied Bio Systems (Darmstadt) |
| siMAPK7 9 | SI00606039 | Qiagen (Hilden, Germany) |
| siMAPK7 10 | SI00606046 | Qiagen (Hilden, Germany) |
| siMAPK7 13 | SI03024924 | Qiagen (Hilden, Germany) |
| siMAPK7 14Q | SI03052980 | Qiagen (Hilden, Germany) |
| siMAZ 3 | SI00628453 | Qiagen (Hilden, Germany) |
| siMAZ 4 | SI00628460 | Qiagen (Hilden, Germany) |
| siMAZ 7 | SI04263945 | Qiagen (Hilden, Germany) |
| siMAZ 8 | SI04352334 | Qiagen (Hilden, Germany) |

-continued

Overview of siRNAs

| Gene symbol +<br>siRNA No. | Catalog No. | Manufacturer |
|---|---|---|
| siPATZ1 2 | SI00771386 | Qiagen (Hilden, Germany) |
| siPATZ1 5 | SI03159051 | Qiagen (Hilden, Germany) |
| siPATZ1 6 | SI03184769 | Qiagen (Hilden, Germany) |
| siPATZ1 7 | SI03208688 | Qiagen (Hilden, Germany) |
| siPCBP3 08 | Silencer ® siRNA, ID #28708 | Applied Bio Systems (Darmstadt) |
| siPCBP3 15 | Silencer ® siRNA, ID #28615 | Applied Bio Systems (Darmstadt) |
| siPCBP3 55 | Silencer ® siRNA, ID #133155 | Applied Bio Systems (Darmstadt) |
| siPDXK 40 | Silencer ® siRNA, ID #440 | Applied Bio Systems (Darmstadt) |
| siPDXK 41 | Silencer ® siRNA, ID #441 | Applied Bio Systems (Darmstadt) |
| siPDXK 42 | Silencer ® siRNA, ID #442 | Applied Bio Systems (Darmstadt) |
| siPIR 09 | Silencer ® siRNA, ID #107209 | Applied Bio Systems (Darmstadt) |
| siPIR 48 | Silencer ® siRNA, ID #115448 | Applied Bio Systems (Darmstadt) |
| siPIR 81 | Silencer ® siRNA, ID #13681 | Applied Bio Systems (Darmstadt) |
| siPPP2CA 10 | Silencer ® siRNA, ID #104510 | Applied Bio Systems (Darmstadt) |
| siPPP2CA 14 | Silencer ® siRNA, ID #104514 | Applied Bio Systems (Darmstadt) |
| siPPP2CA 36 | Silencer ® siRNA, ID #4436 | Applied Bio Systems (Darmstadt) |
| siPRKAA1 94 | Silencer ® siRNA, ID #143194 | Applied Bio Systems (Darmstadt) |
| siPRKAA1 96 | Silencer ® siRNA, ID #242396 | Applied Bio Systems (Darmstadt) |
| siPRKAA1 97 | Silencer ® siRNA, ID #242397 | Applied Bio Systems (Darmstadt) |
| siPSAT1 17 | Silencer ® siRNA, ID #112317 | Applied Bio Systems (Darmstadt) |
| siPTCD1 89 | Silencer ® siRNA, ID #148589 | Applied Bio Systems (Darmstadt) |
| siPTCD1 90 | Silencer ® siRNA, ID #148590 | Applied Bio Systems (Darmstadt) |
| siPTCD1 91 | Silencer ® siRNA, ID #148591 | Applied Bio Systems (Darmstadt) |
| siPTCD1 2 | SI00695338 | Qiagen (Hilden, Germany) |
| siPTCD1 3 | SI00695345 | Qiagen (Hilden, Germany) |
| siPTCD1 4 | SI000695352 | Qiagen (Hilden, Germany) |
| siPTCD1 5 | SI03185350 | Qiagen (Hilden, Germany) |
| siSP1 | siGENOME SMARTpool M-026959-00 | Perbio Science Germany (Bonn, Germany) |
| siTBPL1 58 | Silencer ® siRNA, ID #114458 | Applied Bio Systems (Darmstadt) |
| siTBPL1 59 | Silencer ® siRNA, ID #114459 | Applied Bio Systems (Darmstadt) |
| siTBPL1 60 | Silencer ® siRNA, ID #114460 | Applied Bio Systems (Darmstadt) |
| siTFEB 04 | Silencer ® siRNA, ID #108204 | Applied Bio Systems (Darmstadt) |
| siTFEB 16 | Silencer ® siRNA, ID #6616 | Applied Bio Systems (Darmstadt) |
| siTFEB 19 | Silencer ® siRNA, ID #114719 | Applied Bio Systems (Darmstadt) |

The functional relevance of all potential target proteins was verified using siRNA technology in the eNOS-promoter reporter cell line EA.csr03. For this technology to be used successfully in the eNOS-transcription test, 3-4 commercially available siRNAs with different target sequences, which differed very markedly in their efficiency in the switching-off of their target proteins, were used for each target candidate.

For identification of the best siRNAs, these were transfected in EA.hy926 cells (final concentration 100 nM unless stated otherwise) and after 24 hours the RNA was isolated and purified. The remaining amount of RNA of the respective target was determined quantitatively in RT-PCR in comparison with GAPDH. If a good antibody to the candidate protein existed, the protein expression was analyzed in separate setups 48 hours after siRNA-transfection by lysis of the cells with SDS sample buffer and subsequent Western blotting in comparison with GAPDH.

The point of time for sample generation was selected on the basis of previously conducted kinetic investigations of various siRNAs (data not shown), in which the switching-off reached its peak at the mRNA level 24 h after transfection, and at the protein level after 48 h on account of the subsequent translation.

After identifying the most efficient siRNA for each potential target, it was then used in EA.csr03 cells in the eNOS-transcription test. It was thus possible, through the almost complete switching-off of these proteins, to investigate their role in substance-induced eNOS-transcription enhancement. If the protein investigated had a key function in induced eNOS-transcription enhancement, AVE3085 should no longer be able to activate the eNOS promoter.

4. General Review of all Validated siRNAs and Verification of the Most Efficient Ones in the eNOS-Transcription Test The survey of the efficiencies of different siRNAs to the target proteins were tested. The respective residual mRNA was determined by quantitative RT-PCR, 24 hours after transfection of human endothelial cells (EA.hy926/EA.csr03). Next, the most efficient siRNAs were selected and were used in the eNOS-transcription test. The EA.csr03 cells were treated 48 hours after transfection with AVE3085 (5 µM) for a further 18 h. After cell lysis, the luciferase activity and the total cellular protein content were determined.

As the verification of all siRNAs required the use of several 96-well cell culture plates, The AVE3085-induced reporter gene activity was determined relative to the DMSO-control luciferase activity. Through the switching-off of HEBP1, the eNOS promoter could now only be activated significantly by a factor of 1.6 in comparison with the siLV2-control by a factor of 2.4. Therefore, the HEBP1-protein seems to play a role in AVE3085-mediated eNOS-transcription enhancement.

All the other siRNAs were investigated and evaluated in the eNOS-transcription test. The observed effects on the basal activation state of the promoter and on AVE3085-induced promoter activation are summarized in Table 7.

TABLE 7

Summary of the results of the most efficient siRNAs in the eNOS-transcription test

| siRNA | Residual mRNA after siRNA treatment (siLV2 = 100%) | eNOS basal (siLV2 = 100%) | AVE3085 induction (siLV2 = 100%) |
|---|---|---|---|
| siLV2 |  | 100 ± 5 | 100 ± 5 |
| siPIR 09 | 15 ± 2 | 95 ± 16 | 93 ± 4 |
| siTBPL1 60 | 10 ± 4 | 80 ± 9 | 109 ± 8 |
| siTFEB 04 | 35 ± 4 | 83 ± 3 | 94 ± 3 |
| siPPP2CA 36 | 17 ± 4 | 75 ± 6* | 104 ± 13 |
| siLGALS3 93 | 21 ± 4 | 88 ± 9 | 91 ± 10 |
| siHEBP1 25 | 10 ± 2 | 89 ± 8 | 64 ± 8* |
| siMAPK7 14Q | 27 ± 7 | 64 ± 6* | 93 ± 2 |
| siPCBP3 15 | 19 ± 2 | 78 ± 7 | 111 ± 12 |
| siHTATIP2 72 | 8 ± 1 | 82 ± 4 | 125 ± 13 |
| siCMAS 01 | 7 ± 2 | 81 ± 10 | 103 ± 10 |
| siMAPK3 05 | 6 ± 2 | 90 ± 15 | 114 ± 11 |
| SiIDH3A 44 | 7 ± 2 | 87 ± 11 | 121 ± 11 |
| siPRKAA1 96 | 9 ± 2 | 82 ± 11 | 99 ± 16 |
| siPSAT1 | 7 ± 2 | 82 ± 4 | 97 ± 3 |
| siGLO1 15 | 6 ± 1 | 72 ± 18* | 113 ± 16 |
| siADK 74 | 9 ± 1 | 79 ± 15 | 100 ± 14 |
| siPDXK 42 | 8 ± 1 | 77 ± 7 | 91 ± 11 |
| siPTCD1 3 | 40 ± 22 | 78 ± 1 | 107 ± 4 |

(*p < 0.05 vs. siLV2-control)

Only HEBP1 displayed, after switching-off by siRNA, a significant reduction of eNOS-promoter activation by AVE3085 of 64% versus siLV2-control. It was therefore the only candidate protein that could play a role as target for AVE3085-mediated transcription enhancement.

5. Selection of Efficient siRNAs and Use in the eNOS-Transcription Test with the Example of Heme-Binding Protein 1 (HEBP1)

As already mentioned, HEBP1 was the only protein for which, after switching-off through siRNA, the eNOS promoter could no longer be activated to the same extent as the siLV2-control. Therefore, HEBP1 should be adopted once again as an example of a candidate for eNOS-transcription enhancement by AVE3085.

For transcription test for eNOS promoter activation, 20 000 cells per well of the reporter cell line EA.csr03 were sown in a white 96-well cell culture plate. After 24 hours, various dilutions of the substance in cell culture medium were prepared starting from DMSO stock solutions and were preincubated for 10 min at 37° C. on a water bath. Then these incubation media (100 µl/well) were added to the cells. After incubation for 18 hours, the cells were washed twice with DPBS (100 µl/well) and luciferase lysis buffer (50 µl/well) was added. After 10 min, the solubilized luciferase-substrate luciferin (100 µl/well) was added to the cell lysates. During the luciferase-catalyzed oxidation of luciferin to oxyluciferin there is release of chemiluminescence. The emitted light is a measure of the luciferase activity and hence indirectly a measure of the eNOS-promoter activation. The light units released were measured in the Genios microplate reader from Tecan Deutschland (Crailsheim, Germany).

In experiments in which the EA.csr03 cells were treated with various siRNAs prior to measurement of luciferase activity, sometimes there were slight changes in the numbers of cells on account of toxic effects. Therefore, for standardization of luciferase activity, it was necessary to determine the total protein content of the cell lysates. For this, after treatment the cells were washed twice with 100 µl/well DPBS and dissolved in 60 µl/well of a CHAPS-lysis buffer of HEPES (20 mM, pH 7.4), sodium chloride (150 mM) and 1.1% CHAPS, and shaken for 20 min at room temperature. From each sample, 15 µl of this lysate was removed, transferred to a protein determination plate and diluted with 135 µl water in the ratio 1:10. The total protein content was determined with the Micro BCA protein determination test in accordance with the manufacturer's instructions. In each case 45 µl of doubly-concentrated luciferase cell lysis reagent was added to the remaining 45 µl cell lysate/well and the luciferase activity was determined as described previously.

Statistical analysis of the experimental results was carried out using GraphPad Prism 4.03 software. All the results were presented as mean value+standard deviation. The significance of the results was assessed with a "Student t test". At a p-value of <0.05 the data were deemed to be significant and were indicated in the graphs with "*" or "#".

As in the previously shown validations of various siRNAs, the most efficient HEBP1-siRNA was identified at the mRNA level using quantitative RT-PCR (FIG. 1). In the case of cells treated with siHEBP1 12 and siHEBP1 20, 69% and 40% HEBP1-mRNA, respectively, could still be detected 24 hours after transfection. In contrast, after treatment of the cells with siHEBP1 25 the residual amount of HEBP1-mRNA, at 10% versus siLV2-controls, was very small. Thus, siHEBP1 25 provides a very efficient siRNA for switching off HEBP1 in the cellular context and is very suitable for further use in the eNOS-transcription test. Validation at the protein level was not possible for this potential target, as no functioning antibody was available.

Next, the test conditions used were employed in the eNOS-transcription test (FIG. 2). In siLV2-treated control cells, induction of the eNOS promoter by AVE3085 by a factor of 2.4 versus DMSO-control is possible. If, however, HEBP1 is switched off using siHEBP1 25, the promoter is inducible significantly versus siLV2 only by a factor of 1.6. On the basis of this result, HEBP1 is probably a protein that has a central role in AVE3085-mediated eNOS-transcription enhancement.

Example 4

Biochemical Validation of Heme-Binding Protein 1 (HEBP1) as a Potential Target for eNOS-Transcription Enhancement The heme-binding protein 1 (HEBP1) was the only candidate protein for which, after switching-off the protein by siRNA technology, the activation of the eNOS promoter by AVE3085 was reduced.

The starting situation for further biochemical validation work for HEBP1 was not simple. The only antibody commercially available at this point of time (Abnova GmbH, Heidelberg, Germany, Catalog No. H00050865-A01) showed considerable nonspecificities in Western Blot (data not shown). Recombinant human protein was also not commercially available. Therefore an initial key of further validation work was recombinant expression and purification of human HEBP1.

1. Expression and Purification of Human Heme-Binding Protein 1

To improve purification, HEBP1 was provided with Hexahis-affinity labeling at the N-terminus and was expressed in *E. coli* by recombinant techniques using a previously cloned expression plasmid. The cell pellets from a total of 4 liters of *E. coli* culture were used for each purification run. The Hexahis-HEBP1 was purified as described in the following using a Hexahis-binding affinity material (TALON™ Superflow Metal Affinity Column).

Since human heme-binding protein 1 (HEBP1) is not commercially available, but was required as potential target for further validation of this protein as potential target, it was expressed in *E. coli* by recombinant techniques and then isolated. For cloning of an expression vector for human Hexahis-HEBP1 for *E. coli*, the human HEBP1 gene was amplified in PCR by means of an available expression vector for mammalian cells "huHEBP1-pcDNA3.1", using Phusion™ Hot Start High-Fidelity DNA-polymerase. The human HEBP1 gene was provided with an ecoR1 cleavage site at the 5'-end through primer design. The primers used were

```
                                         SEQ ID NO: 24
forward-EcoR1: 5'-CGTGAATTCGATCAAGAACTCGCTGTTCG-3'

SEQ ID NO: 25
reverse: 5'-TAAACGGGCCCTCTAGACTC-3'
```

The PCR-product obtained was isolated with the QIAquick PCR purification system and was inserted via the EcoRI and XhoI cleavage sites in the "multiple cloning site" (MCS) of the basis vector Champion™ pET302/NT-His by directed ligation. The basis vector used already carries, at the 5'-end of the MCS, the genetic code for Hexahis-affinity labeling and for attachment of the desired protein to the N-terminus.

The vector obtained was transformed into competent JM109 *E. coli* cells, amplified there and the plasmid-DNA was purified with the PureYield™ plasmid preparation system. Finally, the concentration and purity of the DNA was determined in a volume of 2 µl using the NanoDrop® ND-1000 spectrophotometer (NanoDrop Technologies, Wilmington, USA).

Expression of the human protein Hexahis-HEBP1 was carried out using the expression vector for Hexahis-HEBP1 as described. In order to achieve the highest possible protein expression in *E. coli*, the chemically competent strain BL21 Star™ (DE3) was selected. This strain is characterized by a mutation in the gene of the RNase, which is chiefly responsible for the degradation of mRNA transcripts. Owing to the resultant RNase-deficiency, larger amounts of mRNA accumulate, thus leading to a higher protein yield. For protein expression, a 50 µl-aliquot of the competent *E. coli* cells per transformation batch was thawed on ice and 10 ng plasmid-DNA in a volume of 5 µl was added. Incubation on ice for 30 min was followed by heat shock for 30 s at 42° C. on a water bath. Then the cells were put on ice immediately, 250 µl of S.O.C. transformation medium was added, shaking for one hour at 37° C. Then in each case 100 µl was plated on an ampicillin-agar plate, in order to select transformed cells via the ampicillin-resistance gene present on the expression plasmid. The agar plate was incubated overnight at 37° C., then four different clones were inoculated in 5 ml Luria Bertani medium (10 g trypton; 5 g yeast extract; 10 g sodium chloride and water to 1000 ml) with carbenicillin (50 µg/ml) and again cultivated overnight. In each case, glycerol was added to 1 ml of these cultures and this was stored as stock culture at −70° C. The remaining 4 ml of preculture was cultivated in 100 ml of LB medium with carbenicillin (50 µg/ml) up to an optical density of 0.6 at a wavelength of λ=600 nm ($OD_{600}$) and added to 1 mM isopropyl-β-D-thiogalactopyranoside (IPTG), an inductor of the lac-operon in *E. coli*. The IPTG interacts with the repressor LacR and so prevents it binding to the operator. The transcription of the relevant gene is activated. After induction of protein expression by IPTG, the cells were cultivated for a further 4 h. To harvest the cells, the cell suspension was centrifuged in several portions for 15 min at 3000×g/4° C., the medium was removed and the pellets were stored at −20° C. until further use.

The Hexahis-HEBP1 previously expressed in *E. coli* was purified chromatographically using an "ÄKTApurifier" (GE Healthcare Europe, Freiburg, Germany). The column material used for affinity purification was a TALON™ Superflow metal affinity column (Clontech Laboratories, Mountain View, USA). This is an affinity material with positively charged cobalt ions, fixed to Sepharose beads by chelating agents, on its surface. Through the highly specific interaction of the histidine residues with the cobalt ions, recombinant proteins, which are provided with Hexahis labeling, are bound reversibly to the column material and therefore enriched. This principle is called "immobilized metal affinity chromatography" (IMAC). The native protein is eluted with imidazole, which competes with the histidine residues for binding to the cobalt ions.

In each case 20 ml TALON® xTractor buffer per gram of cell pellet was used for lysis of the *E. coli* cells. The cells were carefully resuspended and centrifuged for 20 min at 12 000× g/4° C. to clarify the lysate. The supernatant was removed and was passed through a 0.2 µM sterile filter for complete removal of all particles.

For purification of the Hexahis-HEBP1, the cell lysate was applied to the TALON column, rinsed beforehand with equilibration buffer (pH 7.0) of sodium phosphate (50 mM) and sodium chloride (300 mM), at a flow rate of 0.5 ml/min. The column was rewashed with 10-20 column volumes of equilibration buffer and the bound, Hexahis-labeled HEBP1 was washed from the column with an imidazole-containing elution buffer pH 7.0 consisting of sodium phosphate (50 mM), sodium chloride (300 mM) and imidazole (150 mM). The eluate was collected in 2-ml portions in a fraction collector. With a UV detector with variable wavelengths connected to the column, it was possible to monitor both application of the cell lysate and the elution of Hexahis-HEBP1.

The runthrough and the fractions obtained, which were combined in pairs in each case, were concentrated by centrifugation at 4000×g in Amicon tubes with an exclusion size of 10 kDa. By rinsing in each case with 8 ml dialysis buffer pH 7.4 of HEPES (20 mM) and sodium chloride (100 mM) and additional centrifugation steps, additionally a buffer exchange of the samples was performed, finally concentrating to a final volume of approx. 0.5 ml. Small amounts of the concentrates were taken and SDS samples were prepared for analysis by SDS-PAGE and silver staining or Western blot. The remainder was either used immediately in subsequent experiments or was shock-frozen in liquid nitrogen and stored at −20° C. until further use.

For observation of the elution process, absorption was measured at the wavelengths λ=280 nm and λ=405 nm. The absorption at λ=280 nm is a general measure for protein. Heme-containing proteins show additional absorption at λ=405 nm.

The elution of Hexahis-HEBP1 after addition of imidazole only took place after a certain retention time. Starting from fraction 10 there was a sharp increase in the protein and heme content of the fractions. Elution of the main proportion of the protein could be monitored up to fraction 16, after which there was a continual decrease in protein content. Starting from this fraction, the chromatogram showed a kind of "shoulder" at λ=280 nm, the height of which continued to decrease and by fraction 30 had almost returned to the basal level.

All fractions were combined in pairs and then buffer exchange was carried out with 20 mM HEPES (pH 7.4) and 100 mM sodium chloride to remove any imidazole still present. The samples were concentrated and small amounts were taken for generating SDS samples, the rest being used in subsequent experiments.

The SDS samples generated from the fractions were submitted to gel electrophoresis. For control purposes, a sample of the column runthrough of unbound proteins was also applied. Then silver staining of the protein in the gel or immunodetection of the Hexahis-labeling of the HEBP1 in Western Blot were carried out in parallel.

In silver staining quite large amounts of an approx. 23 kDa protein are discernible in fractions 12-28, and from fraction 16 it is in almost completely pure form. The observed molecular weight is in good agreement with the theoretical value of 21 kDa of HEBP1. A second protein band with a size of approx. 40 kDa is discernible as a slight "contamination" in these fractions, and this might be a dimer of HEBP1.

The result from silver staining was confirmed in immunological detection of the Hexahis-affinity labeling in Western Blot. Very large amounts of Hexahis-labeled HEBP1 with a molecular weight of ~23 kDa were detected in fractions 12 to 28. Once again, a slight "contamination" also with antibody to the Hexahis-labeling was detected at approx. 40 kDa, which might be a further indication of the presence of a dimer. In the run-through, no Hexahis-HEBP1 was recognized by the antibody, i.e. binding of the protein to the column material took place quantitatively.

Based on the results from silver staining and Western Blot, fractions 16-28 with a purity of the HEBP1 of >95% were used in subsequent tests. The protein content of the individual fractions was determined using the BCA method. Generally a total of 8 mg of purified human Hexahis-HEBP1 was obtained from one purification.

2. Binding Studies on 6×His-huHEBP1 by Quenching of Tryptophan Fluorescence

For carrying out binding studies with human HEBP1, it is possible to utilize the intrinsic fluorescence of the tryptophan residues at $\lambda=340$ nm, using an excitation wavelength of $\lambda=295$ nm. The resultant fluorescence can be "quenched" by binding of porphyrins in spatial proximity to the tryptophan residues. This leads to a decrease of intrinsic fluorescence, which therefore provides a measure for the binding of a ligand. In order to optimize the experimental conditions for these quench measurements it was first necessary to evaluate the spectroscopic properties of the recombinant Hexahis-HEBP1.

2.1 Spectroscopic Characterization of Hexahis-HEBP1

An absorption spectrum of HEBP1 (35 µM) using a Nanodrop® photometer showed a strong principal absorption at $\lambda=290$ nm (data not shown). Based on this result, next a HEPES-buffered solution of HEBP1 (0.5 µM) was excited at a wavelength of $\lambda=290$ nm and the resultant emission was determined at various wavelengths.

Measurement of the emission spectrum showed a maximum at a wavelength of $\lambda=340$ nm. To construct an excitation spectrum excitation was carried out at various wavelengths and the emission was measured at a constant wavelength of $\lambda=340$ nm. This spectrum showed an excitation maximum at $\lambda=295$ nm.

The spectroscopic characterization of human Hexahis-HEBP1 is in good agreement with subsequent measurements of tryptophan fluorescence at $\lambda_{exc}=295$ nm and $\lambda_{em}=340$ nm.

2.2 Binding of Hemin and Protoporphyrin IX to Hexahis-HEBP1

Next, studies of the binding of hemin and protoporphyrin IX (PPIX) to human Hexahis-HEBP1 in the presence of eNOS transcription enhancers by tryptophan quenching were carried out. Binding studies with human HEBP1 are carried out using the intrinsic fluorescence of tryptophan residues that are contained. The fluorescence occurring at $\lambda=340$ nm after excitation with a wavelength of $\lambda=295$ nm can be "quenched" through the binding of porphyrins in proximity to the tryptophan residues. The measured fluorescence decreases as a function of the concentration of the ligands. Using nonlinear regression, it is possible to calculate the binding parameters.

Hemin and PPIX at concentrations from 30 nM to 10 µM were added to a buffered HEBP1 solution (500 nM) and after incubation for 10 min the tryptophan fluorescence was measured (FIG. 3). It was not possible to use higher porphyrin concentrations owing to the low solubility in aqueous systems.

A concentration-dependent decrease of fluorescence was observed both for hemin and for PPIX. Nonlinear regression of the values gave $IC_{50}$ values of 3 µM for hemin and 13 µM for PPIX. Hemin therefore proved to be 10 times more potent than PPIX and was used in subsequent experiments.

2.3 Influence of eNOS Transcription Enhancers on the Binding of Hemin to Human Hexahis-HEBP1

The influence of the eNOS-transcription enhancers on tryptophan quenching by hemin was investigated next. In the experiments the recombinant human HEBP1 at a concentration of 500 nM was preincubated on ice for 30 min with the eNOS-substance 9257 versus DMSO-control in a binding buffer (pH 7.4) of HEPES (20 mM), sodium chloride (100 mM) and DTT (1 mM). Black, 96-well plates were used as the reaction vessel. Then hemin or protoporphyrin IX was added at varying concentrations through addition of the 200-fold concentrated DMSO stock solution and incubated for 10 min at room temperature. Finally, the tryptophan fluorescence was measured after previous optimization at $\lambda_{exc}=295$ nm and $\lambda_{em}=340$ nm in the Safire$^2$ microplate reader (Tecan Deutschland, Crailsheim, Germany).

The prototype used was substance 9257, because with respect to AVE9488 and AVE3085 it possesses a higher potency and water solubility and therefore leads to less interference in this test.

First we investigated whether substance 9257 can quench the tryptophan fluorescence of HEBP1. No decrease in fluorescence could be measured (data not shown). Therefore the binding of 9257 was investigated indirectly through competition with hemin. For this, HEBP1 (500 nM) was preincubated with 9257 (10 µM) on ice, versus DMSO-control. After 30 min the hemin was added at varying concentrations of 0.1-10 µM and it was incubated at room temperature for a further 10 min before measuring the tryptophan fluorescence (FIG. 4).

FIG. 4 shows a shift of the hemin binding curve to the right during preincubation with 9257. Calculation of the $IC_{50}$ value of both curves by nonlinear regression gave 3.4 µM for 9257 versus 1.1 µM with the DMSO-control. The $IC_{50}$ value was increased by a factor of 3.1 through the presence of 9257. The eNOS-transcription enhancer 9257 displaces hemin from the binding pocket, without itself quenching the tryptophan fluorescence.

Tryptophan fluorescence test did not prove very suitable for more detailed and extensive investigations. Therefore we next established an alternative method of carrying out binding experiments of the eNOS-transcription enhancers to human HEBP1.

3. Binding Experiments of the eNOS-Transcription Enhancers to Human Hexahis-HEBP1 by Measuring Fluorescence Polarization Further studies of the binding of the eNOS-transcription enhancers to human HEBP1 were carried out using the fluorescence polarization method. Substance A300 was used for this purpose, and was provided covalently with rhodamine labeling via a linker.

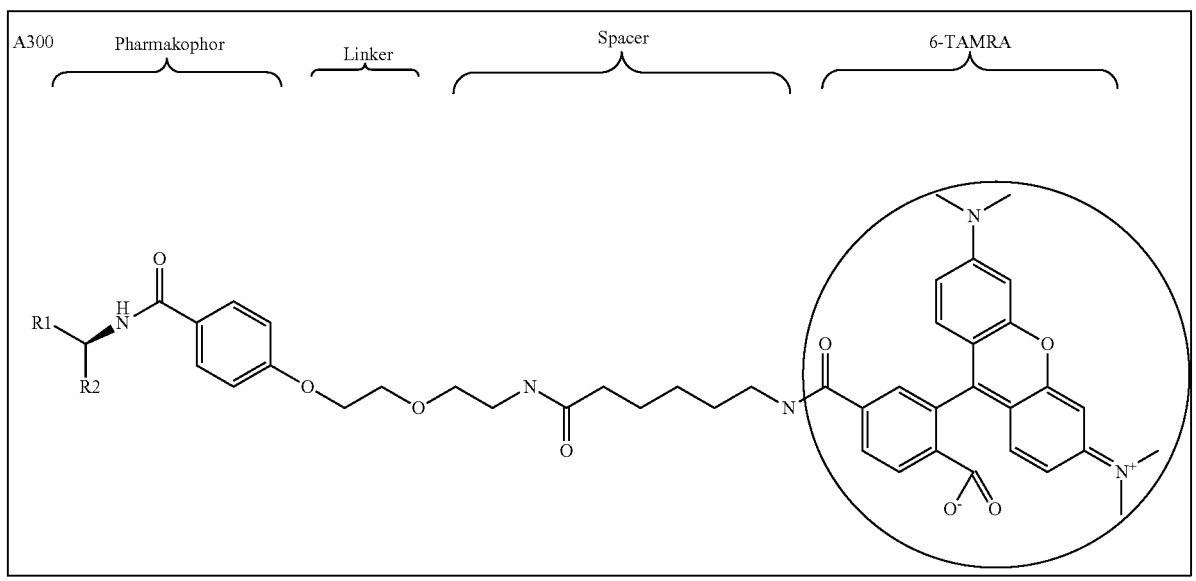

Fluorophores generally emit linearly polarized light, if they are also excited with linearly polarized light. The deflection of this fluorescence polarization depends, however, on the extent to which the fluorophore can rotate between the time of excitation and of emission. If the fluorophore can rotate in space and is not fixed to a binding partner, it emits "isotropically" linearly polarized light through intrinsic rotation at various angles. If, however, the fluorophore is fixed and is no longer able to rotate, it emits the linearly polarized light at a reduced angle ("anisotropy"). This phenomenon can be utilized for measuring the binding of a fluorescence-labeled molecule to a protein. With this measurement principle, prior to excitation in the measuring instrument the incident light is linearly polarized by a polarizer. The fluorescence intensity I of the emitted light is measured in a second polarizer, the so-called "analyzer", at two positions relative to the first polarizer (parallel and perpendicular). The polarization P is defined by the following equation:

$$P = \frac{I_{parallel} - G \cdot I_{perpendicular}}{I_{parallel} + G \cdot I_{perpendicular}}$$

P: polarization
$I_{parallel}$: fluorescence intensity measured when polarizer and analyzer are parallel to one another
$I_{perpendicular}$: fluorescence intensity measured when polarizer and analyzer are perpendicular to one another
G: weighting factor (a factor specific to the instrument)

The polarization P obtained is a dimensionless quantity, which is often stated in mP (=milli-polarization units).

In the present work the fluorescence polarization method was used for conducting binding experiments of the rhodamine-labeled eNOS-substance A300 to recombinant human Hexahis-HEBP1. For sample preparation, various concentrations of the substance A300 with Hexahis-HEBP1 or BSA in a binding buffer (pH 7.4) HEPES (20 mM), sodium chloride (100 mM) and DTT (1 mM) were put on ice. After incubation at room temperature for 10 min, the polarization was measured at an excitation wavelength of λ=530 nm and emission wavelength of λ=585 nm in the Safire² microplate reader (Tecan Deutschland, Crailsheim, Germany). For the experiments carried out here, black 96-well microtiter plates with a glass bottom were used exclusively, as they are characterized by particularly low background fluorescence.

3.1 Activity of the Rhodamine-Labeled Substance A300 in the eNOS-Transcription Test Before the actual biochemical experiments, substance A300 was tested for cellular activity in the eNOS-transcription test versus AVE3085 as reference by determining concentration-effect curves of the test substance. $EC_{50}$ values of 160 nM for A300 and 400 nM for AVE3085 were calculated using nonlinear regression. Therefore, the rhodamine-labeled eNOS-substance A300 had 2.5-times higher cellular activity than the reference and was very suitable for use in binding experiments using the fluorescence polarization method.

3.2 Spectroscopic Characterization of the Rhodamine-Labeled eNOS-Substance A300

First, an absorption spectrum of substance A300 (100 nM) was recorded in a buffered solution, in which an absorption maximum was detected at a wavelength of 555 nm.

A technical limitation of the Safire² microplate reader is that only four defined excitation wavelengths are available for the measurement of fluorescence polarization. However, measurement of emission is possible at any desired wavelength.

The excitation wavelength nearest to the excitation maximum of A300, and available in Safire², was λ=530 nm. For this reason, for validation and quality control of subsequent measurements, an emission spectrum was again recorded with excitation at λ=530 nm.

It was evident from the spectrum recorded that even with this not entirely optimal excitation wavelength, the emission at 585 nm could be measured with high sensitivity. This system could therefore be used for carrying out binding tests of eNOS substances to human Hexahis-HEBP1 using the fluorescence polarization method.

3.3 Binding Studies of the Rhodamine-Labeled eNOS-Substance A300 to Human HEBP1 by the Fluorescence Polarization Method In binding studies, A300 was used as a fluorescence sample at a constant concentration of 30 nM, to which increasing concentrations of HEBP1 were added. To determine the nonspecific portion by general protein binding, parallel experiments were carried out with equal concentrations of bovine serum albumin (BSA). The proportion of specific binding can be estimated from the difference of the binding of A300 to HEBP1 and of the nonspecific binding to BSA (FIG. 5).

The binding curve of A300 to HEBP1 is a typical saturation curve, reaching a plateau with increasing protein concentrations. In contrast, for the binding of A300 to BSA a linear curve is obtained, indicating binding that does not become saturated. By finding the difference in polarization values for the binding of A300 to HEBP1 or BSA, a curve can be computed, with which the proportion of specific binding can be estimated. Using nonlinear regression, a $K_D$ value of 11.7 µM can be calculated for the specific binding of A300 to human Hexahis-HEBP1.

4. Preliminary Studies of HEBP1 Expression in a Pathological Animal Model

In another context, an animal study was conducted, in which rats developed chronic heart failure after an induced myocardial infarction. From available RNA samples from cardiac tissue it was possible to determine the expression of HEBP1_predicted at the mRNA level. The sequence of the HEBP1 gene has not yet been confirmed in the rat, and it was identified by sequence alignment with other species, therefore the designation HEBP1_predicted (NM_001108651) is still used.

Isolation of RNA from the cell types used was carried out using the RNeasy® mini-isolation method. In the first step, a buffer containing guanidine thiocyanate and β-mercaptoethanol (RLT buffer) was added to the cells, which very effectively denatures proteins and in particular inactivates RNases. Cell samples in the 6-well format were in each case dissolved in 600 µl lysis buffer and the viscosity was reduced by centrifugation for 2 min at 14 000×g in QIAshredder columns. By adding 70% (v/v) ethanol, any RNA present is precipitated and binds to the silica membrane of the RNeasy® mini-column. Several washing steps with various buffers are followed by elution of the purified total-RNA with 50 µl nuclease-free water. Cell samples in the 96-well format were in each case dissolved with 140 µl lysis buffer and were then isolated by the RNeasy® mini-isolation method in the BIOROBOT 8000 from Qiagen (Hilden, Germany) according to the manufacturer's instructions. The concentration and purity of the prepared RNA were determined using a Nano-Drop® ND-1000 spectrophotometer (NanoDrop Technologies Inc., Wilmington, USA). In this, from a total volume of 2 µl, the absorption of the samples was measured at a wavelength of λ=260 nm (A260) for nucleic acids. Conversion of the measured absorption to the concentration of the RNA solution was carried out by means of the extinction coefficient of 40 ng×cm$^{-1}$×µl$^{-1}$ on the basis of the Lambert-Beer law. A conclusion about the purity of the RNA is obtained by additional absorption measurement at a wavelength of λ=280 nm (A280), at which proteins, phenols or other impurities absorb. The A260/A280 ratio should be as close as possible to the value of 2 for "pure" RNA. The RNA obtained was then diluted in the ratio 1:5 and either used immediately in a quantitative RT-PCR or stored at −80° C. for future use.

Most of the RNA preparations could be used in quantitative RT-PCR directly, without removing genomic DNA that is still present, as the available probes generally hybridized at an exon-intron junction and so only resultant cDNA was recognized. In the case of probes that did not fulfill this requirement, in accordance with the manufacturer's instructions, DNAse digestion was carried out with the RNase-Free® DNAse set on the RNeasy® mini-column, in conjunction with RNA isolation.

Three different groups each with seven animals were investigated for HEBP1_predicted-expression: one group was sham-operated, i.e. only the abdominal cavity was opened, without inducing a myocardial infarction. Fourteen animals (two groups each of seven animals) developed chronic heart failure after a myocardial infarction was induced. One group was treated for 9 weeks with the eNOS-transcription enhancer AVE3085 at a dose of 10 mg/kg/day versus placebo.

The total-RNA was isolated from the heart and the relative expression of HEBP1-predicted in comparison with GAPDH was determined by quantitative RT-PCR (FIG. 6). The expression data show that on comparing the animals that developed heart failure after myocardial infarction, with the group that underwent the sham operation, there was an increase in expression of HEBP1_predicted by a factor of 2. In contrast, treatment with AVE3085 did not show any influence at all on expression of HEBP1_predicted. HEBP1_predicted appears to play a role in the pathology of this model, since expression was changed.

The invention claimed is:

1. A method of screening for a modulator of endothelial NO synthase (eNOS) expression, the method comprising:
providing a test system comprising a heme binding protein 1 (HEBP1) selected from the group consisting of a recombinant naturally occurring HEBP1, a naturally occurring HEBP1 coupled to at least one marker, and a naturally occurring HEBP1 having deletions at the C-terminus or the N-terminus or both capable of interacting with an eNOS promoter,
contacting the test system with an agent,
indirectly detecting binding of the HEBP1 to the agent by measuring eNOS expression, and
identifying the agent as a modulator of eNOS expression.

2. The method of claim 1, wherein the test system further comprises an eNOS promoter, or one or more transcription factor(s) for the eNOS promoter, or the eNOS promoter and one or more transcription factor(s) for the eNOS promoter.

3. The method of claim 1, wherein the test system comprises a cell.

4. The method of claim 3, wherein the cell is a mammalian cell.

5. The method of claim 3, wherein the cell is a human cell.

6. The method of claim 1, wherein the method is used for screening for a medicament for preventing or treating a disease involving eNOS dysfunction.

7. The method of claim 6, wherein the disease is a cardiovascular disease.

8. The method of claim 6, wherein the disease is myocardial infarction.

9. The method of claim 1, wherein the HEBP1 is human HEBP1.

10. The method of claim 1, wherein the HEBP1 is selected from the group consisting of *Mus musculus, Pan troglodytes, Gallus gallus, Canis familiaris*, and *Rattus norvegicus*.

* * * * *